US008575403B2

(12) United States Patent
Johnston et al.

(10) Patent No.: US 8,575,403 B2
(45) Date of Patent: Nov. 5, 2013

(54) HYDROLYSIS OF ETHYL ACETATE IN ETHANOL SEPARATION PROCESS

(75) Inventors: Victor J. Johnston, Houston, TX (US); Lincoln Sarager, Houston, TX (US); R. Jay Warner, Houston, TX (US); Trinity Horton, Houston, TX (US); Radmila Jevtic, Houston, TX (US)

(73) Assignee: Celanese International Corporation, Dallas, TX (US)

( * ) Notice: Subject to any disclaimer, the term of this patent is extended or adjusted under 35 U.S.C. 154(b) by 174 days.

(21) Appl. No.: 12/833,737

(22) Filed: Jul. 9, 2010

(65) Prior Publication Data

US 2011/0275861 A1    Nov. 10, 2011

Related U.S. Application Data

(60) Provisional application No. 61/332,696, filed on May 7, 2010, provisional application No. 61/332,699, filed on May 7, 2010, provisional application No. 61/332,728, filed on May 7, 2010, provisional application No. 61/346,344, filed on May 19, 2010.

(51) Int. Cl.
*C07C 29/80*    (2006.01)
*C07C 29/147*    (2006.01)

(52) U.S. Cl.
USPC ............ 568/877; 568/884; 568/885; 568/913

(58) Field of Classification Search
USPC ........................................ 568/877, 885, 913
See application file for complete search history.

(56) References Cited

U.S. PATENT DOCUMENTS

| | | |
|---|---|---|
| 1,939,116 A | 12/1933 | Fuchs |
| 2,607,807 A | 8/1952 | Ford |
| 2,649,407 A | 8/1953 | Harrison et al. |
| 2,702,783 A | 2/1955 | Harrison et al. |
| 2,801,209 A | 7/1957 | Muller et al. |
| 2,882,244 A | 4/1959 | Milton |
| 3,102,150 A | 8/1963 | Hunter et al. |
| 3,130,007 A | 4/1964 | Breck |
| 3,408,267 A | 10/1968 | Miller et al. |
| 3,445,345 A | 5/1969 | Katzen et al. |
| 3,478,112 A | 11/1969 | Adam et al. |
| 3,709,795 A | 1/1973 | Singleton |
| 3,769,329 A | 10/1973 | Knox et al. |
| 3,864,284 A | 2/1975 | Clippinger et al. |
| 3,884,981 A | 5/1975 | Kiff |
| 3,925,490 A | 12/1975 | Reich et al. |
| 3,990,952 A | 11/1976 | Katzen et al. |
| 4,008,131 A | 2/1977 | Price |
| 4,039,395 A | 8/1977 | Eby |
| 4,107,002 A | 8/1978 | Eck et al. |
| 4,126,539 A | 11/1978 | Derr, Jr. et al. |
| 4,149,940 A | 4/1979 | Pinto |
| 4,262,154 A | 4/1981 | Gane et al. |
| 4,275,228 A | 6/1981 | Gruffaz et al. |
| 4,306,942 A | 12/1981 | Brush et al. |
| 4,317,918 A | 3/1982 | Takano et al. |
| 4,319,058 A | 3/1982 | Kulprathipanja et al. |
| 4,328,375 A | 5/1982 | Barlow |
| 4,338,221 A | 7/1982 | Qualeatti |
| 4,352,940 A | 10/1982 | Adelman et al. |
| 4,352,947 A | 10/1982 | Habib et al. |
| 4,370,491 A | 1/1983 | Bott et al. |
| 4,379,028 A | 4/1983 | Berg et al. |
| 4,395,576 A | 7/1983 | Kwantes et al. |
| 4,398,039 A | 8/1983 | Pesa et al. |
| 4,409,405 A | 10/1983 | Lin et al. |
| 4,421,939 A | 12/1983 | Kiff et al. |
| 4,422,903 A | 12/1983 | Messick et al. |
| 4,429,056 A | 1/1984 | Smith |
| 4,430,506 A | 2/1984 | Gauthier-Lafaye et al. |
| 4,443,639 A | 4/1984 | Pesa et al. |
| 4,451,677 A | 5/1984 | Bradley et al. |
| 4,454,358 A | 6/1984 | Kummer et al. |
| 4,456,775 A | 6/1984 | Travers |
| 4,465,854 A | 8/1984 | Pond et al. |
| 4,471,136 A | 9/1984 | Larkins et al. |
| 4,476,326 A | 10/1984 | Lin et al. |
| 4,480,115 A | 10/1984 | McGinnis |
| 4,481,146 A | 11/1984 | Leupold et al. |
| 4,492,808 A | 1/1985 | Hagen et al. |
| 4,497,967 A | 2/1985 | Wan |
| 4,514,515 A | 4/1985 | Travers et al. |
| 4,514,521 A | 4/1985 | Smith |
| 4,517,391 A | 5/1985 | Schuster et al. |
| 4,520,213 A | 5/1985 | Victor |
| 4,541,897 A | 9/1985 | Sommer et al. |

(Continued)

FOREIGN PATENT DOCUMENTS

| CA | 1233484 | 3/1988 |
|---|---|---|
| CN | 1230458 | 10/1999 |

(Continued)

OTHER PUBLICATIONS

International Search Report and Written Opinion for PCT/US2011/023276 mailed Sep. 2, 2011 (12 pages).
English Abstract for EP0137749, Apr. 17, 1985.
Zheng, et al.(2007). Preparation and catalytic properties of a bimetallic Sn-Pt complex in the supercages of NaY zeolite by use of surface organometallic chemistry, Applied Organometallic Chemistry, 21(10), 836-840.
ZeaChem, Inc., Technology Overview, Lakewood, Colorado www.zeachem.com, 2008.
Santori et al.(2000). Hydrogenation of carbonylic compounds on Pt/SiO2 catalysts modified with SnBu4, Studies in Surface Science and Catalysis, 130, 2063-2068.
Amit M. Goda et al., (2005). DFT modeling of selective reduction of acetic acid to acetaldehyde on Pt-based bimetallic catalysts, 20th NAM, Houston, TX, Jun. 17-22, 2007 available online at < http://www.nacatsoc.org/20nam/abstracts/O-S9-18.pdf>.

(Continued)

*Primary Examiner* — Sikarl Witherspoon

(57) ABSTRACT

Recovery of ethanol from a crude ethanol product obtained from the hydrogenation of acetic acid by hydrolyzing a portion of the crude ethanol product or one or more derivative streams obtained therefrom. The one or more derivative streams comprise ethyl acetate and the hydrolyzed stream is directly or indirectly fed to the distillation zone or the hydrogenation reactor.

38 Claims, 3 Drawing Sheets

(56) References Cited

U.S. PATENT DOCUMENTS

| | | |
|---|---|---|
| 4,556,644 A | 12/1985 | Erpenbach et al. |
| 4,569,726 A | 2/1986 | Berg et al. |
| 4,611,085 A | 9/1986 | Kitson |
| 4,626,321 A | 12/1986 | Grethlein et al. |
| 4,626,604 A | 12/1986 | Hiles et al. |
| 4,628,130 A | 12/1986 | Bournonville |
| 4,629,711 A | 12/1986 | Erpenbach et al. |
| 4,664,753 A | 5/1987 | Erpenbach et al. |
| 4,678,543 A | 7/1987 | Houben et al. |
| 4,692,218 A | 9/1987 | Houben et al. |
| 4,737,318 A | 4/1988 | Ichino et al. |
| 4,751,334 A | 6/1988 | Turner et al. |
| 4,758,600 A | 7/1988 | Arimitsu et al. |
| 4,762,817 A | 8/1988 | Logsdon et al. |
| 4,777,303 A | 10/1988 | Kitson et al. |
| 4,804,791 A | 2/1989 | Kitson et al. |
| 4,826,795 A | 5/1989 | Kitson et al. |
| 4,837,367 A | 6/1989 | Gustafson et al. |
| 4,837,368 A | 6/1989 | Gustafson et al. |
| 4,842,693 A | 6/1989 | Wheldon |
| 4,876,402 A | 10/1989 | Logsdon et al. |
| 4,886,905 A | 12/1989 | Larkins et al. |
| 4,908,477 A | 3/1990 | Hartmann et al. |
| 4,961,826 A | 10/1990 | Greithlein et al. |
| 4,978,778 A | 12/1990 | Isshiki et al. |
| 4,985,572 A | 1/1991 | Kitson et al. |
| 4,990,655 A | 2/1991 | Kitson et al. |
| 4,992,582 A | 2/1991 | Ruppert et al. |
| 4,994,608 A | 2/1991 | Torrence et al. |
| 5,001,259 A | 3/1991 | Smith et al. |
| 5,004,845 A | 4/1991 | Bradley et al. |
| 5,008,235 A | 4/1991 | Wegman et al. |
| 5,026,908 A | 6/1991 | Smith et al. |
| 5,035,776 A | 7/1991 | Knapp |
| 5,047,592 A | 9/1991 | Carpenter |
| 5,061,671 A | 10/1991 | Kitson et al. |
| 5,070,016 A | 12/1991 | Hallberg |
| 5,124,004 A | 6/1992 | Grethlein et al. |
| 5,137,861 A | 8/1992 | Shih et al. |
| 5,144,068 A | 9/1992 | Smith et al. |
| 5,149,680 A | 9/1992 | Kitson et al. |
| 5,185,476 A | 2/1993 | Gustafson |
| 5,185,481 A | 2/1993 | Muto et al. |
| 5,196,601 A | 3/1993 | Kitsuki et al. |
| 5,198,592 A | 3/1993 | Van Beijnum et al. |
| 5,215,902 A | 6/1993 | Tedder |
| 5,220,020 A | 6/1993 | Buchwald et al. |
| 5,227,141 A | 7/1993 | Kim et al. |
| 5,233,099 A | 8/1993 | Tabata et al. |
| 5,237,108 A | 8/1993 | Marraccini et al. |
| 5,241,106 A | 8/1993 | Inoue et al. |
| 5,243,095 A | 9/1993 | Roberts et al. |
| 5,250,271 A | 10/1993 | Horizoe et al. |
| 5,254,758 A | 10/1993 | Hiles et al. |
| 5,300,685 A | 4/1994 | Scates et al. |
| 5,334,751 A | 8/1994 | Lemanski et al. |
| 5,348,625 A | 9/1994 | Berg |
| 5,362,918 A | 11/1994 | Aizawa et al. |
| 5,399,752 A | 3/1995 | Okrasinski et al. |
| 5,403,962 A | 4/1995 | Schneider et al. |
| 5,414,161 A | 5/1995 | Uhm et al. |
| 5,415,741 A | 5/1995 | Berg |
| 5,416,237 A | 5/1995 | Aubigne et al. |
| 5,426,246 A | 6/1995 | Nagahara et al. |
| 5,437,770 A | 8/1995 | Berg |
| 5,445,716 A | 8/1995 | Berg |
| 5,449,440 A | 9/1995 | Rescalli et al. |
| 5,476,974 A | 12/1995 | Moore et al. |
| 5,480,665 A | 1/1996 | Smith |
| 5,488,185 A | 1/1996 | Ramachandran et al. |
| 5,502,094 A | 3/1996 | Moore et al. |
| 5,502,248 A | 3/1996 | Funk et al. |
| 5,527,969 A | 6/1996 | Kaufhold et al. |
| 5,567,765 A | 10/1996 | Moore et al. |
| RE35,377 E | 11/1996 | Steinberg et al. |
| 5,599,976 A | 2/1997 | Scates et al. |
| 5,658,962 A | 8/1997 | Moore et al. |
| 5,696,284 A | 12/1997 | Baker et al. |
| 5,731,252 A | 3/1998 | Warner et al. |
| 5,747,486 A | 5/1998 | Sohda et al. |
| 5,762,765 A | 6/1998 | Berg |
| 5,770,761 A | 6/1998 | Lin et al. |
| 5,770,770 A | 6/1998 | Kim et al. |
| 5,800,681 A | 9/1998 | Berg |
| 5,821,111 A | 10/1998 | Gaddy et al. |
| 5,831,133 A | 11/1998 | Mimoun |
| 5,861,530 A | 1/1999 | Atkins et al. |
| 5,877,347 A | 3/1999 | Ditzel et al. |
| 5,877,348 A | 3/1999 | Ditzel et al. |
| 5,883,295 A | 3/1999 | Sunley et al. |
| 5,932,764 A | 8/1999 | Morris et al. |
| 5,942,460 A | 8/1999 | Garland et al. |
| 5,955,397 A | 9/1999 | Didillon et al. |
| 5,973,193 A | 10/1999 | Crane et al. |
| 5,977,010 A | 11/1999 | Roberts et al. |
| 5,993,610 A | 11/1999 | Berg |
| 5,998,658 A | 12/1999 | Wu et al. |
| 6,024,176 A | 2/2000 | Moore et al. |
| 6,040,474 A | 3/2000 | Jobson et al. |
| 6,046,127 A | 4/2000 | Mimoun |
| 6,049,008 A | 4/2000 | Roberts et al. |
| 6,093,845 A | 7/2000 | Van Acker et al. |
| 6,121,497 A | 9/2000 | Murphy |
| 6,121,498 A | 9/2000 | Tustin et al. |
| 6,140,535 A | 10/2000 | Williams |
| 6,143,930 A | 11/2000 | Singh et al. |
| 6,204,299 B1 | 3/2001 | Moore et al. |
| 6,214,253 B1 | 4/2001 | Moore et al. |
| 6,232,352 B1 | 5/2001 | Vidalin et al. |
| 6,294,703 B1 | 9/2001 | Hara et al. |
| 6,326,515 B1 | 12/2001 | Clode et al. |
| 6,361,713 B1 | 3/2002 | Moore et al. |
| 6,375,807 B1 | 4/2002 | Nieuwoudt et al. |
| 6,403,840 B1 | 6/2002 | Zhou et al. |
| 6,458,996 B1 | 10/2002 | Muskett |
| 6,462,231 B1 | 10/2002 | Yanagawa et al. |
| 6,462,243 B1 | 10/2002 | Zhou et al. |
| 6,465,696 B1 | 10/2002 | Zhou et al. |
| 6,465,699 B1 | 10/2002 | Grosso |
| 6,472,555 B2 | 10/2002 | Choudary et al. |
| 6,472,572 B1 | 10/2002 | Zhou et al. |
| 6,486,366 B1 | 11/2002 | Ostgard et al. |
| 6,486,368 B1 | 11/2002 | Zhou et al. |
| 6,491,983 B2 | 12/2002 | Moore et al. |
| 6,495,730 B1 | 12/2002 | Konishi et al. |
| 6,509,180 B1 | 1/2003 | Verser |
| 6,509,290 B1 | 1/2003 | Vaughn et al. |
| 6,525,230 B2 | 2/2003 | Grosso |
| 6,552,220 B1 | 4/2003 | Obana et al. |
| 6,627,770 B1 | 9/2003 | Cheung et al. |
| 6,632,330 B1 | 10/2003 | Colley et al. |
| 6,657,078 B2 | 12/2003 | Scates et al. |
| 6,670,490 B1 | 12/2003 | Campos et al. |
| 6,685,754 B2 | 2/2004 | Kindig et al. |
| 6,693,213 B1 | 2/2004 | Kolena et al. |
| 6,696,596 B1 | 2/2004 | Herzog et al. |
| 6,713,655 B2 | 3/2004 | Yilmaz et al. |
| 6,723,886 B2 | 4/2004 | Allison et al. |
| 6,755,975 B2 | 6/2004 | Vane et al. |
| 6,765,110 B2 | 7/2004 | Warner et al. |
| 6,768,021 B2 | 7/2004 | Horan et al. |
| 6,809,217 B1 | 10/2004 | Colley et al. |
| 6,863,211 B2 | 3/2005 | Moore et al. |
| 6,867,164 B2 | 3/2005 | Obana et al. |
| 6,903,045 B2 | 6/2005 | Zoeller et al. |
| 6,906,228 B2 | 6/2005 | Fischer et al. |
| 6,927,048 B2 | 8/2005 | Verser |
| 7,005,541 B2 | 2/2006 | Cheung et al. |
| 7,019,182 B2 | 3/2006 | Grosso |
| 7,074,603 B2 | 7/2006 | Verser |
| 7,084,312 B1 | 8/2006 | Huber et al. |
| 7,091,155 B2 | 8/2006 | Inui et al. |
| 7,115,772 B2 | 10/2006 | Picard et al. |
| 7,148,390 B2 | 12/2006 | Zhou et al. |

(56) References Cited

U.S. PATENT DOCUMENTS

| | | |
|---|---|---|
| 7,161,050 B2 | 1/2007 | Sherman et al. |
| 7,208,624 B2 | 4/2007 | Scates et al. |
| 7,223,886 B2 | 5/2007 | Scates et al. |
| 7,230,150 B2 | 6/2007 | Grosso et al. |
| 7,297,236 B1 | 11/2007 | Vander et al. |
| 7,351,559 B2 | 4/2008 | Verser |
| 7,361,794 B2 | 4/2008 | Grosso |
| 7,375,049 B2 | 5/2008 | Hayes et al. |
| 7,399,892 B2 | 7/2008 | Rix et al. |
| 7,507,562 B2 | 3/2009 | Verser |
| 7,538,060 B2 | 5/2009 | Barnicki et al. |
| 7,553,397 B1 | 6/2009 | Colley et al. |
| 7,572,353 B1 | 8/2009 | Vander et al. |
| 7,601,865 B2 | 10/2009 | Verser |
| 7,608,744 B1 | 10/2009 | Johnston et al. |
| 7,652,167 B2 | 1/2010 | Miller et al. |
| 7,667,068 B2 | 2/2010 | Miller et al. |
| 7,678,940 B2 | 3/2010 | Miura et al. |
| 7,682,812 B2 | 3/2010 | Verser |
| 7,700,814 B2 | 4/2010 | Garton et al. |
| 7,725,657 B2 | 5/2010 | Hasenplaugh et al. |
| 7,732,173 B2 | 6/2010 | Mairal et al. |
| 7,744,727 B2 | 6/2010 | Blum et al. |
| 7,820,852 B2 | 10/2010 | Johnston et al. |
| 7,834,223 B2 | 11/2010 | Atkins et al. |
| 7,838,708 B2 | 11/2010 | Sherman et al. |
| 7,842,844 B2 | 11/2010 | Atkins |
| 7,863,489 B2 | 1/2011 | Johnston |
| 7,884,253 B2 | 2/2011 | Stites |
| 7,888,082 B2 | 2/2011 | Verser |
| 7,906,680 B2 | 3/2011 | Scates et al. |
| 7,947,746 B2 | 5/2011 | Daniel et al. |
| 7,964,379 B2 | 6/2011 | Verser et al. |
| 7,994,368 B2 | 8/2011 | Johnston et al. |
| 8,071,821 B2 | 12/2011 | Johnston et al. |
| 2001/0027172 A1 | 10/2001 | Moore et al. |
| 2002/0156328 A1 | 10/2002 | Grosso |
| 2002/0198416 A1 | 12/2002 | Zhou et al. |
| 2003/0004057 A1 | 1/2003 | Yamaguchi et al. |
| 2003/0013908 A1 | 1/2003 | Horan et al. |
| 2003/0069452 A1 | 4/2003 | Sherman et al. |
| 2003/0077771 A1 | 4/2003 | Verser et al. |
| 2003/0078456 A1 | 4/2003 | Yilmaz et al. |
| 2003/0104587 A1 | 6/2003 | Verser et al. |
| 2003/0114719 A1 | 6/2003 | Fischer et al. |
| 2003/0120121 A1 | 6/2003 | Sherman et al. |
| 2003/0125585 A1 | 7/2003 | Yilmaz et al. |
| 2003/0125589 A1 | 7/2003 | Grosso |
| 2003/0135069 A1 | 7/2003 | Fujita et al. |
| 2003/0153059 A1 | 8/2003 | Pilkington et al. |
| 2003/0166973 A1 | 9/2003 | Zhou et al. |
| 2004/0006246 A1 | 1/2004 | Sherman et al. |
| 2004/0009614 A1 | 1/2004 | Ahn et al. |
| 2004/0063184 A1 | 4/2004 | Grichko |
| 2004/0152915 A1 | 8/2004 | Fujita et al. |
| 2004/0232049 A1 | 11/2004 | Dath et al. |
| 2004/0242917 A1 | 12/2004 | Inui et al. |
| 2004/0267074 A1 | 12/2004 | Grosso et al. |
| 2005/0043572 A1 | 2/2005 | Grosso |
| 2005/0192468 A1 | 9/2005 | Sherman et al. |
| 2005/0209328 A1 | 9/2005 | Allgood et al. |
| 2005/0214408 A1 | 9/2005 | Pilkington et al. |
| 2006/0019360 A1 | 1/2006 | Verser et al. |
| 2006/0127999 A1 | 6/2006 | Verser et al. |
| 2006/0224013 A1 | 10/2006 | Inui et al. |
| 2006/0247466 A1 | 11/2006 | Zinobile et al. |
| 2006/0252956 A1 | 11/2006 | Miller et al. |
| 2007/0031954 A1 | 2/2007 | Mairal et al. |
| 2007/0106246 A1 | 5/2007 | Modesitt |
| 2007/0144886 A1 | 6/2007 | Sylvester et al. |
| 2007/0265360 A1 | 11/2007 | Luo et al. |
| 2007/0270511 A1 | 11/2007 | Melnichuk et al. |
| 2008/0103335 A1 | 5/2008 | Scates et al. |
| 2008/0135396 A1 | 6/2008 | Blum |
| 2008/0187472 A1 | 8/2008 | Ahn et al. |
| 2008/0193989 A1 | 8/2008 | Verser |
| 2008/0207953 A1 | 8/2008 | Houssin et al. |
| 2008/0257784 A1 | 10/2008 | Dath et al. |
| 2008/0269518 A1 | 10/2008 | Scates et al. |
| 2009/0005588 A1 | 1/2009 | Hassan et al. |
| 2009/0014313 A1 | 1/2009 | Lee et al. |
| 2009/0023192 A1 | 1/2009 | Verser et al. |
| 2009/0069609 A1 | 3/2009 | Kharas |
| 2009/0081749 A1 | 3/2009 | Verser et al. |
| 2009/0099389 A1 | 4/2009 | Shaver |
| 2009/0166172 A1 | 7/2009 | Casey et al. |
| 2009/0221725 A1 | 9/2009 | Chornet et al. |
| 2009/0264285 A1 | 10/2009 | Luo et al. |
| 2009/0270651 A1 | 10/2009 | Zinobile et al. |
| 2009/0281354 A1 | 11/2009 | Mariansky et al. |
| 2009/0299092 A1 | 12/2009 | Beavis et al. |
| 2009/0318573 A1 | 12/2009 | Stites et al. |
| 2009/0326080 A1 | 12/2009 | Chornet et al. |
| 2009/0326268 A1 | 12/2009 | Hanes et al. |
| 2010/0016454 A1 | 1/2010 | Gracey et al. |
| 2010/0029980 A1 | 2/2010 | Johnston et al. |
| 2010/0029993 A1 | 2/2010 | Johnston et al. |
| 2010/0029995 A1 | 2/2010 | Johnston et al. |
| 2010/0029996 A1 | 2/2010 | Danjo et al. |
| 2010/0030001 A1 | 2/2010 | Chen et al. |
| 2010/0030002 A1 | 2/2010 | Johnston et al. |
| 2010/0041919 A1 | 2/2010 | Wu et al. |
| 2010/0063319 A1 | 3/2010 | Brtko et al. |
| 2010/0069515 A1 | 3/2010 | Tirtowidjojo et al. |
| 2010/0080736 A1 | 4/2010 | Hassan et al. |
| 2010/0121114 A1 | 5/2010 | Weiner et al. |
| 2010/0121119 A1 | 5/2010 | Sherman et al. |
| 2010/0137630 A1 | 6/2010 | Garton et al. |
| 2010/0145097 A1 | 6/2010 | Brtko et al. |
| 2010/0168493 A1 | 7/2010 | Le Peltier et al. |
| 2010/0185021 A1 | 7/2010 | Ross et al. |
| 2010/0196789 A1 | 8/2010 | Fisher et al. |
| 2010/0197485 A1 | 8/2010 | Johnston et al. |
| 2010/0197959 A1 | 8/2010 | Johnston |
| 2010/0197985 A1 | 8/2010 | Johnston et al. |
| 2010/0204512 A1 | 8/2010 | Kimmich et al. |
| 2010/0249479 A1 | 9/2010 | Berg-Slot et al. |
| 2010/0261800 A1 | 10/2010 | Daniel et al. |
| 2010/0273229 A1 | 10/2010 | Verser |
| 2010/0311138 A1 | 12/2010 | Padgett |
| 2011/0004033 A1 | 1/2011 | Johnston et al. |
| 2011/0004034 A1 | 1/2011 | Daniel et al. |
| 2011/0034741 A1 | 2/2011 | Sherman et al. |
| 2011/0046421 A1 | 2/2011 | Daniel et al. |
| 2011/0082322 A1 | 4/2011 | Jevtic et al. |
| 2011/0098501 A1 | 4/2011 | Johnston |
| 2011/0185628 A1 | 8/2011 | Johnston et al. |
| 2011/0190547 A1 | 8/2011 | Jevtic et al. |
| 2011/0190548 A1 | 8/2011 | Jevtic et al. |
| 2011/0190552 A1 | 8/2011 | Powell et al. |
| 2011/0224462 A1 | 9/2011 | Ditzel et al. |
| 2011/0263911 A1 | 10/2011 | Johnston et al. |
| 2011/0275861 A1 | 11/2011 | Johnston |
| 2011/0275862 A1 | 11/2011 | Johnston et al. |
| 2012/0010438 A1 | 1/2012 | Lee et al. |
| 2012/0010445 A1 | 1/2012 | Johnston et al. |

FOREIGN PATENT DOCUMENTS

| | | |
|---|---|---|
| CN | 1944373 | 4/2007 |
| CN | 1944374 | 4/2007 |
| CN | 101665424 | 3/2010 |
| CN | 201768393 | 3/2011 |
| CN | 102228831 | 11/2011 |
| CN | 102229520 | 11/2011 |
| DE | 241590 | 12/1986 |
| DE | 60025239 | 6/2006 |
| EP | 0056488 | 7/1982 |
| EP | 0087870 | 9/1983 |
| EP | 0104197 | 4/1984 |
| EP | 0137749 | 4/1985 |
| EP | 0167300 A1 | 1/1986 |
| EP | 0175558 | 3/1986 |
| EP | 0192587 | 8/1986 |

(56) References Cited

FOREIGN PATENT DOCUMENTS

| | | |
|---|---|---|
| EP | 0198682 | 10/1986 |
| EP | 0285420 | 10/1988 |
| EP | 0285786 | 10/1988 |
| EP | 0400904 | 5/1990 |
| EP | 0372847 | 6/1990 |
| EP | 0456647 | 11/1991 |
| EP | 0535825 | 5/1996 |
| EP | 0944572 | 9/1999 |
| EP | 0990638 | 4/2000 |
| EP | 0992482 | 4/2000 |
| EP | 1338587 | 8/2003 |
| EP | 2060553 A1 | 5/2009 |
| EP | 2060555 A1 | 5/2009 |
| EP | 2072487 | 6/2009 |
| EP | 2072488 | 6/2009 |
| EP | 2072489 | 6/2009 |
| EP | 2072492 | 6/2009 |
| EP | 2186787 | 5/2010 |
| GB | 2053915 | 2/1981 |
| JP | 60-09454 | 1/1985 |
| JP | 60-25033 | 2/1985 |
| JP | 61-28181 | 2/1986 |
| JP | 02-215790 | 8/1990 |
| JP | 4-193304 | 7/1992 |
| JP | 51-86391 | 7/1993 |
| JP | 6-116182 | 4/1994 |
| JP | 2001-046874 | 2/2001 |
| JP | 2001-157841 | 6/2001 |
| JP | 2005-289936 | 10/2005 |
| KR | 2012 0010763 | 2/2012 |
| WO | WO 82/03854 | 11/1982 |
| WO | WO 83/03409 | 10/1983 |
| WO | WO 98/25876 | 6/1998 |
| WO | WO 2002/092541 | 11/2002 |
| WO | WO 2005/102513 | 11/2005 |
| WO | WO 2007/003897 | 1/2007 |
| WO | WO 2008/135192 | 11/2008 |
| WO | WO 2009/009320 | 1/2009 |
| WO | WO 2009/009322 | 1/2009 |
| WO | WO 2009/009323 | 1/2009 |
| WO | WO 2009/048335 | 4/2009 |
| WO | WO 2009/063174 | 5/2009 |
| WO | WO 2009/063176 | 5/2009 |
| WO | WO 2009/077719 | 6/2009 |
| WO | WO 2009/077720 | 6/2009 |
| WO | WO 2009/077725 | 6/2009 |
| WO | WO 2009/077729 | 6/2009 |
| WO | WO 2009/103948 | 8/2009 |
| WO | WO 2009/105860 | 9/2009 |
| WO | WO 2010/014145 | 2/2010 |
| WO | WO 2010/014151 | 2/2010 |
| WO | WO 2010/014153 | 2/2010 |
| WO | WO 2010/030320 | 3/2010 |
| WO | WO 2010/055285 | 5/2010 |
| WO | WO 2011/053365 | 5/2011 |
| WO | WO 2011/056597 | 5/2011 |
| WO | WO 2011/097193 | 8/2011 |
| WO | WO 2011/097208 | 8/2011 |
| WO | WO 2011/097217 | 8/2011 |
| WO | WO 2011/097219 | 8/2011 |
| WO | WO 2011/140455 | 11/2011 |
| WO | WO 2012/006228 | 1/2012 |
| WO | WO 2012/006388 | 1/2012 |
| WO | WO 2012/006499 | 1/2012 |

OTHER PUBLICATIONS

Acala, et al.,(2005). Experimental and DFT studies of the conversion of ethanol and acetic acid on PtSn-based catalysts, Journal of Physical Chemistry, 109(6), 2074-2085.

Written Opinion mailed May 8, 2012 in corresponding International Application No. PCT/US2011/023276.

International Search Report and Written Opinion mailed on Aug. 11, 2011 in corresponding International Application No. PCT/US2011/023283.

Written Opinion mailed on Jan. 30, 2012 in corresponding International Application No. PCT/US2011/023283.

International Search Report and Written Opinion mailed Sep. 6, 2011 in corresponding International Application No. PCT/US2011/023338.

Invitation to Pay Additional Fees and Partial Search Report mailed May 4, 2011 in corresponding International Application No. PCT/US2011/023283.

International Preliminary Report on Patentability mailed May 18, 2012 in corresponding International Application No. PCT/US2011/023283.

Written Opinion mailed May 16, 2012 in corresponding International Application No. PCT/US2011/023338.

Claus, et al., "Selective Hydrogenolysis of methyl and ethyl acetate in the gas phase on copper and supported Group VIII metal catalysts", Applied Catalysis A, 79, 1991, p. 1-18.

Pallasana et al., "Reaction Paths in the Hydrogenolysis of Acetic Acid to Ethanol over Pd(111), Re(0001), and RdRe Alloys", Journal of Catalysis, 209, Mar. 1, 2002, pp. 289-305.

International Search Report and Written Opinion mailed May 31, 2012 in corresponding International Application No. PCT/US2011/043213.

Witzeman and Agreda in "Acetic Acid and its Derivatives,", Marcel Dekker, NY, 1992, p. 271.

International Preliminary Report on Patentability for PCT/US2011/023276 mailed Jun. 27, 2012.

International Preliminary Report on Patentability for PCT/US2011/023338 mailed on Jul. 5, 2012.

Invitation to Pay Additional Fees and Partial Search Report for PCT/US2011/043213 mailed Feb. 23, 2012.

International Search Report and Written Opinion mailed Jun. 11, 2012 in corresponding International Application No. PCT/US2012/020977.

Gursahani et al., "Reaction kinetics measurements and analysis of reaction pathways for conversions of acetic acid, ethanol, and ethyl acetate over silica-supported Pt", Applied Catalysis A: General 222 (2001) 369-392.

Invitation to Pay Fees mailed Mar. 13, 2012 in corresponding International Application No. PCT/US2012/020977.

International Search Report and Written Opinion mailed Mar. 14, 2012 in corresponding International Application No. PCT/US2012/020979.

Pestman et al., Identification of the Active Sites in the Selective Hydrogenation of Acetic Acid to Acetaldehyde on Iron Oxide Catalysts, Journal of Catalysis 174:142-152 (1998).

International Search Report and Written Opinion for PCT/US2011/043310 dated Feb. 23, 2012.

Subramani et al. "A Review of Recent Literature to Search for an Efficient Catalytic Process for the Conversion of Syngas to Ethanol," Energy & Fuels, 2008, vol. 22, pp. 814-839.

Spivey et al., "Heterogeneous catalytic synthesis of ethanol from biomass-dervied syngas," Chemical Society Review, 2007, vol. 36, pp. 1514-1528.

Michael Gauβ, et al., Applied Homogeneous Catalysis with Organometallic Compounds: A Comprehensive Handbook in two Volume, Chapter 2.1, p. 27-200, (1st ed., 1996).

Juran et al., "Convert Methanol to Ethanol", Hydrocarbon Processing, Oct. 1985, pp. 85-87.

Zhang et al., "Hydrogenation of Ethyl Acetate to Ethanol over Ni-Based Catalysts Obtained from Ni/Al Hydrotalcite-Like Compounds", Molecules, 2010, 15, 5139-5152.

International Search Report and Written Opinion mailed Jul. 12, 2012 in corresponding International Application No. PCT/US2012/035166.

Rachmady, Acetic Acid Reduction by H2 on Bimetallic Pt-Fe Catalysts, Journal of Catalysis 209, 87-98, Apr. 1, 2002, Elsevier Science (USA).

J. Jones, et al., "The Cativa™ Process for the Manufacture of Acetic Acid", Platinum Metals Review, vol. 44, No. 3, pp. 94-104 (Jul. 2000).

Hilmen, Separation of Azeotropic Mixtures: Tools for Analysis and Studies on Batch Distillation Operation (Nov. 2000) pp. 17-20.

(56) References Cited

OTHER PUBLICATIONS

International Search Report and Written Opinion mailed Jul. 6, 2012 in corresponding International Application No. PCT/US2011/059889.

Marian Simo et al., "Adsorption/Desorption of Water and Ethanol on 3A Zeolite in Near-Adiabatic Fixed Bed", Ind. Eng. Chem. Res., 2009, 48, 9247-9260.

N. Calvar et al., "Esterification of acetic acid with ethanol: Reaction kinetics and operation in a packed bed reactive distillation column", Chemical Engineering and Processing, 46 (207) 1317-1323.

Hidetoshi Kita et al., "Synthesis of a zeolite NaA membrane for pervaporation of water/organic liquid mixtures", Journal of Materials Science Letters, 14 (1995) 206-208.

International Search Report and Written Opinion mailed Jul. 30, 2012 in corresponding International Application No. PCT/US2012/035189.

International Search Report and Written Opinion mailed Aug. 20, 2012 in corresponding International Application No. PCT/US2011/046498.

International Search Report and Written Opinion mailed Aug. 2, 2012 in corresponding International Application No. PCT/US2012/035220.

International Search Report and Written Opinion mailed Jul. 30, 2012 in corresponding International Application No. PCT/US2012/035273.

Tracy J. Benson et al., "Cellulose Based Adsorbent Materials for the Dehydration of Ethanol Using Thermal Swing Adsorption", vol. 11, 2005, pp. 697-701.

Yu Huang et al., "Low-Energy Distillation-Membrane Separation Process", Ind. Eng. Chem. Res., vol. 49, 2010, pp. 3760-3768.

International Search Report and Written Opinion mailed Aug. 6, 2012 in corresponding International Application No. PCT/US2012/035196.

Anonymous, "Studies in Extractive and Azeotropic Distillation Series; Study No. 4—Separation of Alcohols from the Acetate/Alcohol/Water Ternary by Extractive Distillation", May 9, 2008, XP 55033135, pp. 1-9.

V. Ragaini et al., "Increasing the value of dilute acetic acid streams through esterification Part I. Experimental analysis of the reaction zone", Applied Catalysis B: Environmental, vol. 64, 2006, pp. 66-71.

International Search Report and Written Opinion mailed Jul. 30, 2012 in corresponding International Application No. PCT/US2011/059891.

International Search Report and Written Opinion mailed Jul. 11, 2012 in corresponding International Application No. PCT/US2012/035203.

Yang et al, "Process of Ethanol Synthesis through esterification of acetic acid and economic analysis", No. 4, 2011, pp. 1-15.

T. Yokoyama et al., "Carboxylic Acids and Derivatives", Fine Chemicals through Heterogenous Catalysis, pp. 370-379.

S. Ordonez et al., "The role of metal and support sites on the hydrogenation of acetic acid on Ru-based catalysts", 21st NAM San Francisco, CA, Jun. 10, 2009.

Burkhanov et al., "Palladium-Based Alloy Membranes for Separation of High Purity Hydrogen from Hydrogen-Containing Gas Mixtures", Platinum Metals Rev., 2011, vol. 1, pp. 3-12.

HYDROLYSIS OF ETHYL ACETATE IN ETHANOL SEPARATION PROCESS

CROSS REFERENCE TO RELATED APPLICATIONS

This application claims priority to U.S. Provisional Application No. 61/332,696, entitled "Process For Recovering Ethanol," filed on May 7, 2010, U.S. Provisional Application No. 61/332,699, entitled "Process For Purifying Ethanol," filed on May 7, 2010; U.S. Provisional Application No. 61/332,728, entitled "Process For Purifying A Crude Ethanol Product," filed on May 7, 2010, and U.S. Provisional Application No. 61/346,344, entitled "Process For Producing Ethanol Using An Extractive Distillation Column," filed on May 19, 2010, the entireties of which are incorporated herein by reference.

FIELD OF THE INVENTION

The present invention relates generally to processes for producing ethanol and, in particular, to reducing ethyl acetate byproducts by hydrolysis.

BACKGROUND OF THE INVENTION

Ethanol for industrial use is conventionally produced from petrochemical feed stocks, such as oil, natural gas, or coal, from feed stock intermediates, such as syngas, or from starchy materials or cellulose materials, such as corn or sugar cane. Conventional methods for producing ethanol from petrochemical feed stocks, as well as from cellulose materials, include the acid-catalyzed hydration of ethylene, methanol homologation, direct alcohol synthesis, and Fischer-Tropsch synthesis. Instability in petrochemical feed stock prices contributes to fluctuations in the cost of conventionally produced ethanol, making the need for alternative sources of ethanol production all the greater when feed stock prices rise. Starchy materials, as well as cellulose material, are converted to ethanol by fermentation. However, fermentation is typically used for consumer production of ethanol for fuels or consumption. In addition, fermentation of starchy or cellulose materials competes with food sources and places restraints on the amount of ethanol that can be produced for industrial use.

Ethanol production via the reduction of alkanoic acids and/or other carbonyl group-containing compounds has been widely studied, and a variety of combinations of catalysts, supports, and operating conditions have been mentioned in the literature. During the reduction of alkanoic acid, e.g., acetic acid, other compounds are formed with ethanol or are formed in side reactions. These impurities limit the production and recovery of ethanol from such reaction mixtures. For example, during hydrogenation, esters are produced that together with ethanol and/or water form azeotropes, which are difficult to separate. In addition when conversion is incomplete, unreacted acid remains in the crude ethanol product, which must be removed to recover ethanol.

Therefore, a need remains for improving the recovery of ethanol from a crude product obtained by reducing alkanoic acids, such as acetic acid, and/or other carbonyl group-containing compounds.

SUMMARY OF THE INVENTION

In a first embodiment, the present invention is directed to a process for purifying a crude ethanol product comprising: hydrogenating acetic acid in a reactor in the presence of a catalyst to form a crude ethanol product, separating at least a portion of the crude ethanol product in a first column into a first distillate comprising ethanol, water and ethyl acetate, and a first residue comprising acetic acid, separating at least a portion of the first distillate in a second column into a second distillate comprising ethyl acetate and a second residue comprising ethanol and water, optionally separating at least a portion of the second residue in a third column into a third distillate comprising ethanol and a third residue comprising water, optionally separating at least a portion of the second distillate in a fourth column into a fourth distillate comprising acetaldehyde and a fourth residue comprising ethyl acetate, and hydrolyzing at least a portion of one of the first distillate, the second distillate, or the fourth residue to form a hydrolyzed stream.

In a second embodiment, the present invention is directed to a process for purifying a crude ethanol product comprising: hydrogenating acetic acid in a reactor in the presence of a catalyst to form a crude ethanol product, separating at least a portion of the crude ethanol product in a first column into a first distillate comprising ethanol, water, and ethyl acetate, and a first residue comprising acetic acid, separating at least a portion of the first distillate in a second column into a second distillate comprising ethyl acetate and a second residue comprising ethanol and water, optionally separating at least a portion of the second residue in a third column into a third distillate comprising ethanol and a third residue comprising water, and hydrolyzing at least a portion of one of the first distillate or the second distillate to form a hydrolyzed stream.

In a third embodiment, the present invention is directed to a process for purifying a crude ethanol product comprising: hydrogenating acetic acid in a reactor in the presence of a catalyst to form a crude ethanol product, separating at least a portion of the crude ethanol product in a first column into a first distillate comprising ethanol, water, and ethyl acetate, and a first residue comprising acetic acid, separating at least a portion of the first distillate in a second column into a second distillate comprising ethyl acetate and a second residue comprising ethanol and water, optionally separating at least a portion of the second residue in a third column into a third distillate comprising ethanol and a third residue comprising water, separating at least a portion of the second distillate in a fourth column into a fourth distillate comprising acetaldehyde and a fourth residue comprising ethyl acetate, and hydrolyzing at least a portion of the fourth residue to form a hydrolyzed stream.

In a fourth embodiment, the present invention is directed to a process for purifying a crude ethanol product comprising the steps of providing a crude ethanol product comprising ethanol, water, acetic acid, and ethyl acetate, separating at least a portion of the crude ethanol product in a first column into a first distillate comprising ethanol, water and ethyl acetate, and a first residue comprising acetic acid, separating at least a portion of the first distillate in a second column into a second distillate comprising ethyl acetate and a second residue comprising ethanol and water, optionally separating at least a portion of the second residue in a third column into a third distillate comprising ethanol and a third residue comprising water, optionally separating at least a portion of the second distillate in a fourth column into a fourth distillate comprising acetaldehyde and a fourth residue comprising ethyl acetate, and hydrolyzing at least a portion of one of the first distillate, the second distillate, or the fourth residue to form a hydrolyzed stream.

The hydrolysis of the first distillate or the second distillate may be conducted under liquid phase or gas phase condition, preferably under liquid phase conditions. The liquid phase hydrolysis reaction may be conducted in a hydrolysis unit, such as an ion exchange reactor bed, or in a reactive distillation column. The ion exchange reactor bed may comprise a strongly acidic heterogeneous or homogenous catalyst. Preferably, the ion exchange reactor bed is located externally to the distillation columns.

Preferably, the hydrolyzed stream comprises acetic acid and ethanol. The hydrolyzed stream may also comprise ethyl acetate, preferably in an amount less than that of the stream fed to the hydrolysis unit. The amount of ethanol in the hydrolyzed stream is preferably at least 0.5% more, e.g., at least 2% more or at least 4% more, as compared to the stream fed to the hydrolysis unit. The amount of ethyl acetate in the hydrolyzed stream is preferably at least 1% less, e.g., at least 3% less or at least 10% less, as compared to the stream fed to the hydrolysis unit.

In a fifth embodiment, the present invention is directed to a process for hydrolyzing ethyl acetate, comprising hydrogenating acetic acid in a reactor in the presence of a catalyst to form a crude ethanol product, and hydrolyzing an ethyl acetate-containing stream in a hydrolysis unit under conditions effective to form a hydrolyzed stream comprising less ethyl acetate than the ethyl acetate-containing stream, wherein the ethyl acetate-containing stream is the crude ethanol product or a derivative stream thereof.

The hydrolyzed stream preferably is directly or indirectly returned to the reaction zone or distillation zone. When returned to the reaction zone, the hydrolyzed stream may be fed to the vaporizer and/or reactor. When returned to the distillation zone, the hydrolyzed stream may be fed to the flasher and/or first column, e.g., acid separation column.

In one embodiment, water may also be fed to the hydrolysis unit. Preferably the water is a portion of the third residue. Water may also be obtained from an external source. The molar ratio of water to ethyl acetate fed to the hydrolysis unit is preferably at least 2:1, e.g., at least 5:1, at least 10:1, or at least 25:1.

In a sixth embodiment, the present invention is directed to a process for purifying a crude ethanol product comprising: hydrogenating acetic acid in a reactor in the presence of a catalyst to form a crude ethanol product, hydrolyzing at least a portion of the crude ethanol product in a first column, and separating at least a portion of the crude ethanol product in the first column into a first distillate comprising ethanol, water, and a reduced amount of ethyl acetate, and a first residue comprising acetic acid.

BRIEF DESCRIPTION OF DRAWINGS

The invention may be more completely understood in consideration of the following detailed description of various embodiments of the invention in connection with the accompanying drawings, wherein like numerals designate similar parts.

DETAILED DESCRIPTION OF THE INVENTION

Figure 1A:
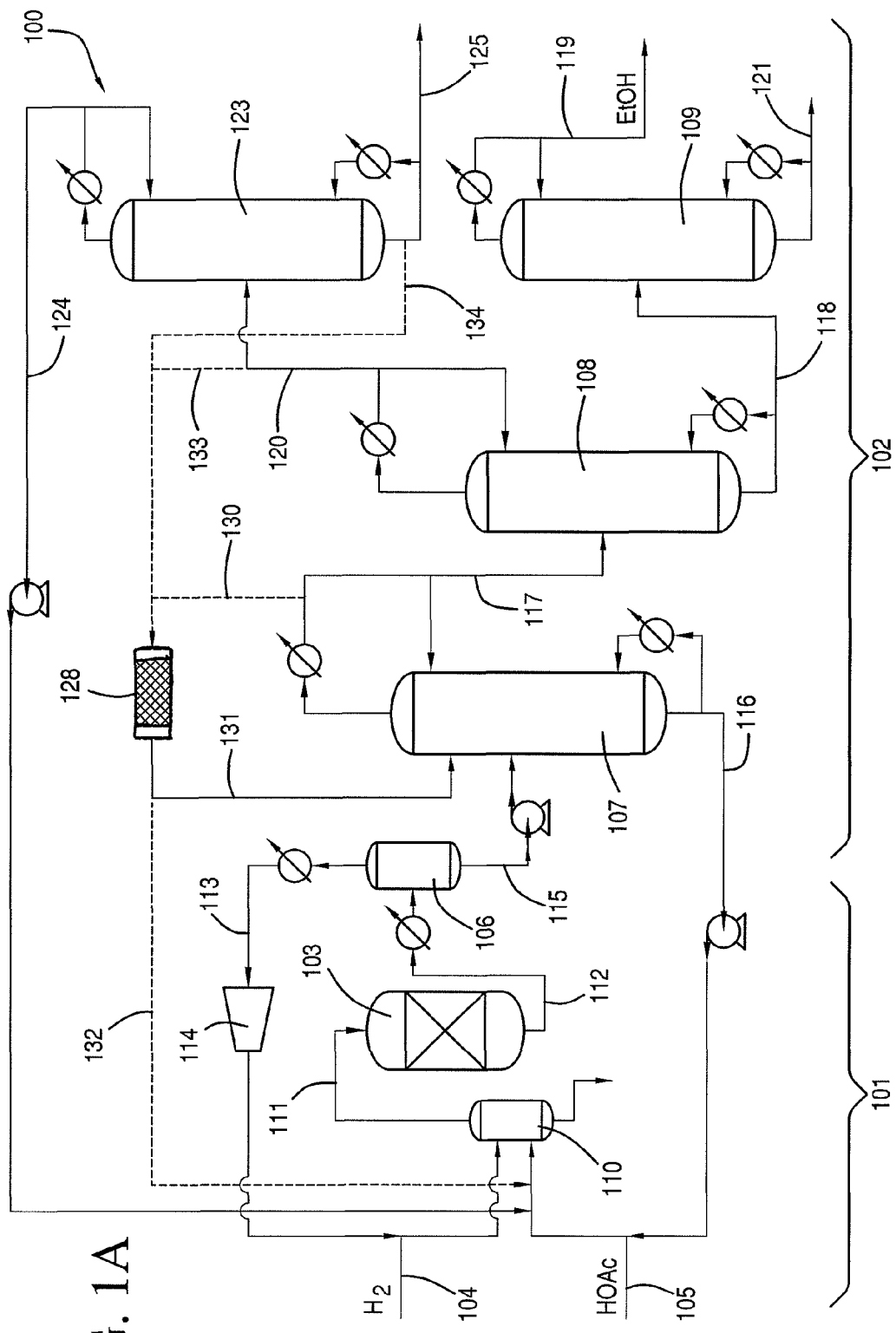
FIG. 1A is a schematic diagram of an ethanol production system having an ion exchange resin reactor bed in accordance with one embodiment of the present invention.

The present invention relates generally to recycling processes in ethanol production systems wherein a stream comprising ethyl acetate is hydrolyzed to form acetic acid and ethanol. Embodiments of the present invention preferably maximize ethanol yields and may also reduce waste streams that are purged from the system.

The process of the present invention can be applied to a variety of ethanol production systems and beneficially may be used in applications for the recovery and/or purification of ethanol on an industrial scale. For example, various aspects of the present invention relate to processes for recovering and/or purifying ethanol produced by a process comprising hydrogenating acetic acid in the presence of a catalyst. In such embodiments, byproduct ethyl acetate, which is present in the crude ethanol product and/or a derivative stream of the crude product, is hydrolyzed using water. The water may be derived from a process stream. Controlled removal of the acetic acid is critical for driving the ethyl acetate hydrolysis reaction to completion in order to achieve higher conversion and increase elimination of ethyl acetate.

The hydrogenation of acetic acid to form ethanol and water may be represented by the following reaction:

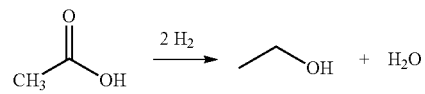

In theoretical embodiments where ethanol and water are the only products of the hydrogenation reaction, the crude ethanol product comprises 71.9 wt. % ethanol and 28.1 wt. % water. However, not all of the acetic acid fed to the hydrogenation reactor is typically converted to ethanol. Subsequent reactions of ethanol, such as esterification, may form other byproducts such as ethyl acetate. Ethyl acetate is a byproduct that reduces the yield of ethanol of the process and increases the waste that must be taken out of the system.

The esterification reaction that produces ethyl acetate has liquid phase equilibrium constant of $K_{est}=4.0$. (See, for example, Witzeman and Agreda in, "Acetic Acid and its Derivatives", Marcel Dekker, NY, 1992, p. 271, the entirety of which is incorporated herein by reference.) The hydrolysis of ethyl acetate has an equilibrium constant, $K_{hyd}=0.25$, which is the reciprocal of the $K_{est}$.

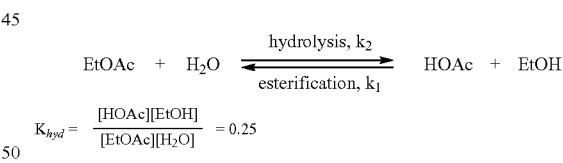

Until the excess acetic acid, which is not converted to products in the hydrogenation reactor, is substantially removed from the crude ethanol product, e.g., in an acid separation column, the crude ethanol product is not at chemical equilibrium and the composition favors esterification of ethanol with acetic acid to form ethyl acetate and water. In one embodiment of the present invention, substantially all of the excess acetic acid is removed. One or more derivative streams that are formed in the separation system may contain small amounts of acetic acid. As such, any mixture of ethanol, ethyl acetate and water in the derivative streams are not at chemical equilibrium, and the hydrolysis of ethyl acetate is thermodynamically favored.

In one embodiment, one or more of the derivative streams obtained by recovering and/or purifying a crude ethanol product is hydrolyzed. In preferred embodiments, the derivative stream to be hydrolyzed comprises ethyl acetate, ethanol, and water. Each of the components in the derivative stream may be obtained from separate streams and mixed. In addition, the one or more derivative streams to be hydrolyzed preferably comprise substantially no acetic acid, e.g., less than 2 wt. % or less than 0.5 wt %. Although ethyl acetate may be hydrolyzed in the absence of a catalyst, it is a preferred that a catalyst is employed to increase reaction rate. In one embodiment, the hydrolysis of the ethyl acetate is performed under liquid phase or gas phase conditions. In one embodiment, the hydrolysis of the ethyl acetate is performed continuously under liquid phase conditions.

According to one embodiment of the invention, the derivative stream is passed through a hydrolysis unit comprising an ion exchange resin reactor bed. The ion exchange resin reactor bed may comprise a strongly acidic heterogeneous or homogenous catalyst, such as for example a Lewis acid, strongly acidic ion exchange catalyst, inorganic acids, and methanesulfonic acid. Exemplary catalysts include Amberlyst™ 15 (Rohm and Haas Company, Philadelphia, U.S.A.), Amberlyst™ 70, Dowex-M-31 (Dow Chemical Company), Dowex Monosphere M-31 (Dow Chemical Company), and Purolite CT type Catalysts (Purolite International SRL). The ion exchange resin reactor bed preferably is a gel or marco-reticular bed. Ion exchange resin reactor beds may be located externally to the distillation columns or within a distillation column. The outflow of the ion exchange resin reactor bed may be directly or indirectly returned to one of the flashers and/or one of the distillation columns, e.g., the acid removal column. In one embodiment, when the system employs two or more flashers, the outflow of the ion exchange resin reactor bed is preferably directed to the low pressure flasher. Optionally, a portion of the outflow of the ion exchange resin reactor bed is fed, along with acetic acid, to the reaction zone.

In one embodiment, the crude ethanol product is fed to a distillation column and ethyl acetate present in the crude ethanol product is hydrolyzed within the distillation column. The distillation column may comprise a reactive distillation column. The distillation column may comprise a hydrolyzing section, preferably in the upper portion of the column or near the top of the column. The hydrolyzing section may comprise an internal ion exchange resin reactor bed. In another embodiment, the hydrolyzing section is an enlarged portion of the column, i.e., has a greater cross-sectional diameter than the lower half of the column. This may increase the residence time of the light boiling point materials in the column to facilitate further hydrolysis of ethyl acetate.

In further embodiments, one or more of the derivative streams may also be fed to the distillation column having the hydrolyzing section. This may allow a derivative stream containing ethyl acetate to be hydrolyzed along with the crude ethanol product. Optionally, the derivative stream may be passed through an external ion exchange resin reactor bed before being fed to the distillation column having the hydrolyzing section.

In one embodiment of the invention, other compounds may also be hydrolyzed with the ethyl acetate, such as diethyl acetate (DEA).

1. Hydrogenation Process

Suitable hydrogenation catalysts include catalysts comprising a first metal and optionally one or more of a second metal, a third metal or additional metals, optionally on a catalyst support. The first and optional second and third metals may be selected from Group IB, IIB, IIIB, IVB, VB, VIIB, VIIB, VIII transitional metals, a lanthanide metal, an actinide metal or a metal selected from any of Groups IIIA, IVA, VA, and VIA. Preferred metal combinations for some exemplary catalyst compositions include platinum/tin, platinum/ruthenium, platinum/rhenium, palladium/ruthenium, palladium/rhenium, cobalt/palladium, cobalt/platinum, cobalt/chromium, cobalt/ruthenium, silver/palladium, copper/palladium, nickel/palladium, gold/palladium, ruthenium/rhenium, and ruthenium/iron. Exemplary catalysts are further described in U.S. Pat. No. 7,608,744 and U.S. Publication No. 2010/0029995, the entireties of which are incorporated herein by reference. Additional catalysts are described in U.S. application Ser. No. 12/698,968, entitled "Catalysts for Making Ethanol from Acetic Acid," filed on Feb. 2, 2010, the entirety of which is incorporated herein by reference.

In one exemplary embodiment, the catalyst comprises a first metal selected from the group consisting of copper, iron, cobalt, nickel, ruthenium, rhodium, palladium, osmium, iridium, platinum, titanium, zinc, chromium, rhenium, molybdenum, and tungsten. Preferably, the first metal is selected from the group consisting of platinum, palladium, cobalt, nickel, and ruthenium. More preferably, the first metal is selected from platinum and palladium. When the first metal comprises platinum, it is preferred that the catalyst comprises platinum in an amount less than 5 wt. %, e.g., less than 3 wt. % or less than 1 wt. %, due to the high demand for platinum.

As indicated above, the catalyst optionally further comprises a second metal, which typically would function as a promoter. If present, the second metal preferably is selected from the group consisting of copper, molybdenum, tin, chromium, iron, cobalt, vanadium, tungsten, palladium, platinum, lanthanum, cerium, manganese, ruthenium, rhenium, gold, and nickel. More preferably, the second metal is selected from the group consisting of copper, tin, cobalt, rhenium, and nickel. More preferably, the second metal is selected from tin and rhenium.

If the catalyst includes two or more metals, e.g., a first metal and a second metal, the first metal optionally is present in the catalyst in an amount from 0.1 to 10 wt. %, e.g., from 0.1 to 5 wt. %, or from 0.1 to 3 wt. %. The second metal preferably is present in an amount from 0.1 and 20 wt. %, e.g., from 0.1 to 10 wt. %, or from 0.1 to 5 wt. %. For catalysts comprising two or more metals, the two or more metals may be alloyed with one another or may comprise a non-alloyed metal solution or mixture.

The preferred metal ratios may vary depending on the metals used in the catalyst. In some exemplary embodiments, the mole ratio of the first metal to the second metal is from 10:1 to 1:10, e.g., from 4:1 to 1:4, from 2:1 to 1:2, from 1.5:1 to 1:1.5 or from 1.1:1 to 1:1.1.

The catalyst may also comprise a third metal selected from any of the metals listed above in connection with the first or second metal, so long as the third metal is different from the first and second metals. In preferred aspects, the third metal is selected from the group consisting of cobalt, palladium, ruthenium, copper, zinc, platinum, tin, and rhenium. More preferably, the third metal is selected from cobalt, palladium, and ruthenium. When present, the total weight of the third metal preferably is from 0.05 and 4 wt. %, e.g., from 0.1 to 3 wt. %, or from 0.1 to 2 wt. %.

In addition to one or more metals, the exemplary catalysts further comprise a support or a modified support, meaning a support that includes a support material and a support modifier, which adjusts the acidity of the support material. The total weight of the support or modified support, based on the total weight of the catalyst, preferably is from 75 wt. % to 99.9 wt. %, e.g., from 78 wt. % to 97 wt. %, or from 80 wt. % to 95 wt. %. In preferred embodiments that use a modified support, the support modifier is present in an amount from 0.1 wt. % to 50 wt. %, e.g., from 0.2 wt. % to 25 wt. %, from 0.5 wt. % to 15 wt. %, or from 1 wt. % to 8 wt. %, based on the total weight of the catalyst.

Suitable support materials may include, for example, stable metal oxide-based supports or ceramic-based supports. Preferred supports include silicaceous supports, such as silica, silica/alumina, a Group IIA silicate such as calcium metasilicate, pyrogenic silica, high purity silica, and mixtures thereof. Other supports may include, but are not limited to, iron oxide, alumina, titania, zirconia, magnesium oxide, carbon, graphite, high surface area graphitized carbon, activated carbons, and mixtures thereof.

In the production of ethanol, the catalyst support may be modified with a support modifier. Preferably, the support modifier is a basic modifier that has a low volatility or no volatility. Such basic modifiers, for example, may be selected from the group consisting of: (i) alkaline earth oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. In addition to oxides and metasilicates, other types of modifiers including nitrates, nitrites, acetates, and lactates may be used. Preferably, the support modifier is selected from the group consisting of oxides and metasilicates of any of sodium, potassium, magnesium, calcium, scandium, yttrium, and zinc, as well as mixtures of any of the foregoing. Preferably, the support modifier is a calcium silicate, and more preferably calcium metasilicate ($CaSiO_3$). If the support modifier comprises calcium metasilicate, it is preferred that at least a portion of the calcium metasilicate is in crystalline form.

A preferred silica support material is SS61138 High Surface Area (HSA) Silica Catalyst Carrier from Saint Gobain NorPro. The Saint-Gobain NorPro SS61138 silica contains approximately 95 wt. % high surface area silica; a surface area of about 250 $m^2/g$; a median pore diameter of about 12 nm; an average pore volume of about 1.0 $cm^3/g$ as measured by mercury intrusion porosimetry and a packing density of about 0.352 $g/cm^3$ (22 $lb/ft^3$).

A preferred silica/alumina support material is KA-160 (Sud Chemie) silica spheres having a nominal diameter of about 5 mm, a density of about 0.562 g/ml, in absorptivity of about 0.583 g $H_2O$/g support, a surface area of about 160 to 175 $m^2/g$, and a pore volume of about 0.68 ml/g.

As will be appreciated by those of ordinary skill in the art, support materials are selected such that the catalyst system is suitably active, selective and robust under the process conditions employed for the formation of ethanol.

The metals of the catalysts may be dispersed throughout the support, coated on the outer surface of the support (egg shell) or decorated on the surface of the support.

The catalyst compositions suitable for use with the present invention preferably are formed through metal impregnation of the modified support, although other processes such as chemical vapor deposition may also be employed. Such impregnation techniques are described in U.S. Pat. No. 7,608,744, U.S. Publication No. 2010/0029995, and U.S. application Ser. No. 12/698,968, referred to above, the entireties of which are incorporated herein by reference.

Some embodiments of the process of hydrogenating acetic acid to form ethanol according to one embodiment of the invention may include a variety of configurations using a fixed bed reactor or a fluidized bed reactor, as one of skill in the art will readily appreciate. In many embodiments of the present invention, an "adiabatic" reactor can be used; that is, there is little or no need for internal plumbing through the reaction zone to add or remove heat. In other embodiments, radial flow reactor or reactors may be employed, or a series of reactors may be employed with or with out heat exchange, quenching, or introduction of additional feed material. Alternatively, a shell and tube reactor provided with a heat transfer medium may be used. In many cases, the reaction zone may be housed in a single vessel or in a series of vessels with heat exchangers therebetween.

In preferred embodiments, the catalyst is employed in a fixed bed reactor, e.g., in the shape of a pipe or tube, where the reactants, typically in the vapor form, are passed over or through the catalyst. Other reactors, such as fluid or ebullient bed reactors, can be employed. In some instances, the hydrogenation catalysts may be used in conjunction with an inert material to regulate the pressure drop of the reactant stream through the catalyst bed and the contact time of the reactant compounds with the catalyst particles.

The hydrogenation reaction may be carried out in either the liquid phase or vapor phase. Preferably, the reaction is carried out in the vapor phase under the following conditions. The reaction temperature may range from 125° C. to 350° C., e.g., from 200° C. to 325° C., from 225° C. to 300° C., or from 250° C. to 300° C. The pressure may range from 10 KPa to 3000 KPa (about 1.5 to 435 psi), e.g., from 50 KPa to 2300 KPa, or from 100 KPa to 1500 KPa. The reactants may be fed to the reactor at a gas hourly space velocity (GHSV) of greater than 500 $hr^{-1}$, e.g., greater than 1000 $hr^{-1}$, greater than 2500 $hr^{-1}$ or even greater than 5000 $hr^{-1}$. In terms of ranges the GHSV may range from 50 $hr^{-1}$ to 50,000 $hr^{-1}$, e.g., from 500 $hr^{-1}$ to 30,000 $hr^{-1}$, from 1000 $hr^{-1}$ to 10,000 $hr^{-1}$, or from 1000 $hr^{-1}$ to 6500 $hr^{-1}$.

The hydrogenation optionally is carried out at a pressure just sufficient to overcome the pressure drop across the catalytic bed at the GHSV selected, although there is no bar to the use of higher pressures, it being understood that considerable pressure drop through the reactor bed may be experienced at high space velocities, e.g., 5000 $hr^{-1}$ or 6,500 $hr^{-1}$.

Although the reaction consumes two moles of hydrogen per mole of acetic acid to produce one mole of ethanol, the actual molar ratio of hydrogen to acetic acid in the feed stream may vary from about 100:1 to 1:100, e.g., from 50:1 to 1:50, from 20:1 to 1:2, or from 12:1 to 1:1. Most preferably, the molar ratio of hydrogen to acetic acid is greater than 2:1, e.g., greater than 4:1 or greater than 8:1.

Contact or residence time can also vary widely, depending upon such variables as amount of acetic acid, catalyst, reactor, temperature, and pressure. Typical contact times range from a fraction of a second to more than several hours when a catalyst system other than a fixed bed is used, with preferred contact times, at least for vapor phase reactions, of from 0.1 to 100 seconds, e.g., from 0.3 to 80 seconds or from 0.4 to 30 seconds.

The raw materials, acetic acid and hydrogen, used in connection with the process of this invention may be derived from any suitable source including natural gas, petroleum, coal, biomass, and so forth. As examples, acetic acid may be produced via methanol carbonylation, acetaldehyde oxidation, ethylene oxidation, oxidative fermentation, and anaerobic fermentation. As petroleum and natural gas prices fluctuate becoming either more or less expensive, methods for producing acetic acid and intermediates such as methanol and carbon monoxide from alternate carbon sources have drawn increasing interest. In particular, when petroleum is relatively expensive compared to natural gas, it may become advantageous to produce acetic acid from synthesis gas ("syn gas") that is derived from any available carbon source. U.S. Pat. No.

6,232,352, the disclosure of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syn gas is diverted from the methanol synthesis loop and supplied to a separator unit to recover CO and hydrogen, which are then used to produce acetic acid. In addition to acetic acid, such a process can also be used to make hydrogen which may be utilized in connection with this invention.

Methanol carbonylation processes suitable for production of acetic acid are described in U.S. Pat. Nos. 7,208,624, 7,115,772, 7,005,541, 6,657,078, 6,627,770, 6,143,930, 5,599,976, 5,144,068, 5,026,908, 5,001,259, and 4,994,608, the disclosure of which is incorporated herein by reference. Optionally, the production of ethanol may be integrated with such methanol carbonylation processes.

U.S. Pat. No. RE 35,377 also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form synthesis gas. The syn gas is converted to methanol which may be carbonylated to acetic acid. The method likewise produces hydrogen which may be used in connection with this invention as noted above. U.S. Pat. No. 5,821,111, which discloses a process for converting waste biomass through gasification into synthesis gas as well as U.S. Pat. No. 6,685,754, the disclosures of which are incorporated herein by reference.

In one optional embodiment, the acetic acid fed to the hydrogenation reaction may also comprise other carboxylic acids and anhydrides, as well as acetaldehyde and acetone. These other compounds may also be hydrogenated in the processes of the present invention. In some embodiments, the present of carboxylic acids, such as propanoic acid or its anhydride, may be beneficial in producing propanol.

Alternatively, acetic acid in vapor form may be taken directly as crude product from the flash vessel of a methanol carbonylation unit of the class described in U.S. Pat. No. 6,657,078, the entirety of which is incorporated herein by reference. The crude vapor product, for example, may be fed directly to the ethanol synthesis reaction zones of the present invention without the need for condensing the acetic acid and light ends or removing water, saving overall processing costs.

The acetic acid may be vaporized at the reaction temperature, following which the vaporized acetic acid may be fed along with hydrogen in an undiluted state or diluted with a relatively inert carrier gas, such as nitrogen, argon, helium, carbon dioxide and the like. For reactions run in the vapor phase, the temperature should be controlled in the system such that it does not fall below the dew point of acetic acid. In one embodiment the acetic acid may be vaporized at the boiling point of acetic acid at the particular pressure, and then the vaporized acetic acid may be further heated to the reactor inlet temperature. In another embodiment, the acetic acid is transferred to the vapor state by passing hydrogen, recycle gas, another suitable gas, or mixtures thereof through the acetic acid at a temperature below the boiling point of acetic acid, thereby humidifying the carrier gas with acetic acid vapors, followed by heating the mixed vapors up to the reactor inlet temperature. Preferably, the acetic acid is transferred to the vapor by passing hydrogen and/or recycle gas through the acetic acid at a temperature at or below 125° C., followed by heating of the combined gaseous stream to the reactor inlet temperature.

In particular, the hydrogenation of acetic acid may achieve favorable conversion of acetic acid and favorable selectivity and productivity to ethanol. For purposes of the present invention, the term "conversion" refers to the amount of acetic acid in the feed that is converted to a compound other than acetic acid. Conversion is expressed as a mole percentage based on acetic acid in the feed. The conversion may be at least 10%, e.g., at least 20%, at least 40%, at least 50%, at least 60%, at least 70% or at least 80%. Although catalysts that have high conversions are desirable, such as at least 80% or at least 90%, in some embodiments a low conversion may be acceptable at high selectivity for ethanol. It is, of course, well understood that in many cases, it is possible to compensate for conversion by appropriate recycle streams or use of larger reactors, but it is more difficult to compensate for poor selectivity.

Selectivity is expressed as a mole percent based on converted acetic acid. It should be understood that each compound converted from acetic acid has an independent selectivity and that selectivity is independent from conversion. For example, if 50 mole % of the converted acetic acid is converted to ethanol, we refer to the ethanol selectivity as 50%. Preferably, the catalyst selectivity to ethoxylates is at least 60%, e.g., at least 70%, or at least 80%. As used herein, the term "ethoxylates" refers specifically to the compounds ethanol, acetaldehyde, and ethyl acetate. Preferably, the selectivity to ethanol is at least 80%, e.g., at least 85% or at least 88%. Preferred embodiments of the hydrogenation process also have low selectivity to undesirable products, such as methane, ethane, and carbon dioxide. The selectivity to these undesirable products preferably is less than 4%, e.g., less than 2% or less than 1%. More preferably, these undesirable products are not detectable. Formation of alkanes may be low, and ideally less than 2%, less than 1%, or less than 0.5% of the acetic acid passed over the catalyst is converted to alkanes, which have little value other than as fuel.

The term "productivity," as used herein, refers to the grams of a specified product, e.g., ethanol, formed during the hydrogenation based on the kilograms of catalyst used per hour. A productivity of at least 200 grams of ethanol per kilogram catalyst per hour, e.g., at least 400 grams of ethanol per kilogram catalyst per hour or at least 600 grams of ethanol per kilogram catalyst per hour, is preferred. In terms of ranges, the productivity preferably is from 200 to 3,000 grams of ethanol per kilogram catalyst per hour, e.g., from 400 to 2,500 per kilogram catalyst per hour or from 600 to 2,000 per kilogram catalyst per hour.

In various embodiments, the crude ethanol product produced by the hydrogenation process, before any subsequent processing, such as purification and separation, will typically comprise unreacted acetic acid, ethanol and water. As used herein, the term "crude ethanol product" refers to any composition comprising from 5 to 70 wt. % ethanol and from 5 to 35 wt. % water. In some exemplary embodiments, the crude ethanol product comprises ethanol in an amount from 5 wt. % to 70 wt. %, e.g., from 10 wt. % to 60 wt. %, or from 15 wt. % to 50 wt. %, based on the total weight of the crude ethanol product. Preferably, the crude ethanol product contains at least 10 wt. % ethanol, at least 15 wt. % ethanol or at least 20 wt. % ethanol. The crude ethanol product typically will further comprise unreacted acetic acid, depending on conversion, for example, in an amount of less than 90 wt. %, e.g., less than 80 wt. % or less than 70 wt. %. In terms of ranges, the unreacted acetic acid is preferably from 0 to 90 wt. %, e.g., from 5 to 80 wt. %, from 15 to 70 wt. %, from 20 to 70 wt. % or from 25 to 65 wt. %. As water is formed in the reaction process, water will generally be present in the crude ethanol product, for example, in amounts ranging from 5 to 35 wt. %, e.g., from 10 to 30 wt. % or from 10 to 26 wt. %. Ethyl acetate may also be produced during the hydrogenation of acetic acid or through side reactions and may be present, for example, in amounts ranging from 0 to 20 wt. %, e.g., from 0 to 15 wt. %, from 1 to 12 wt. % or from 3 to 10 wt. %. Acetaldehyde may also be produced through side reactions and may be present, for example, in amounts ranging from 0 to 10 wt. %, e.g., from 0 to 3 wt. %, from 0.1 to 3 wt. % or from 0.2 to 2 wt. %. Other components, such as, for example, esters, ethers, aldehydes, ketones, alkanes, and carbon dioxide, if detectable, collectively may be present in amounts less than 10 wt. %, e.g., less than 6 wt. % or less than 4 wt. %. In terms of ranges, other components may be present in an amount from 0.1 to 10 wt. %, e.g., from 0.1 to 6 wt. %, or from 0.1 to 4 wt. %. Exemplary embodiments of crude ethanol compositional ranges are provided in Table 1.

TABLE 1

CRUDE ETHANOL PRODUCT COMPOSITIONS

| Component | Conc. (wt. %) | Conc. (wt. %) | Conc. (wt. %) | Conc. (wt. %) |
|---|---|---|---|---|
| Ethanol | 5 to 70 | 10 to 60 | 15 to 50 | 25 to 50 |
| Acetic Acid | 0 to 90 | 5 to 80 | 15 to 70 | 20 to 70 |
| Water | 5 to 35 | 5 to 30 | 10 to 30 | 10 to 26 |
| Ethyl Acetate | 0 to 20 | 0 to 15 | 1 to 12 | 3 to 10 |
| Acetaldehyde | 0 to 10 | 0 to 3 | 0.1 to 3 | 0.2 to 2 |
| Others | 0.1 to 10 | 0.1 to 6 | 0.1 to 4 | — |

2. Purification System

Figure 1B:
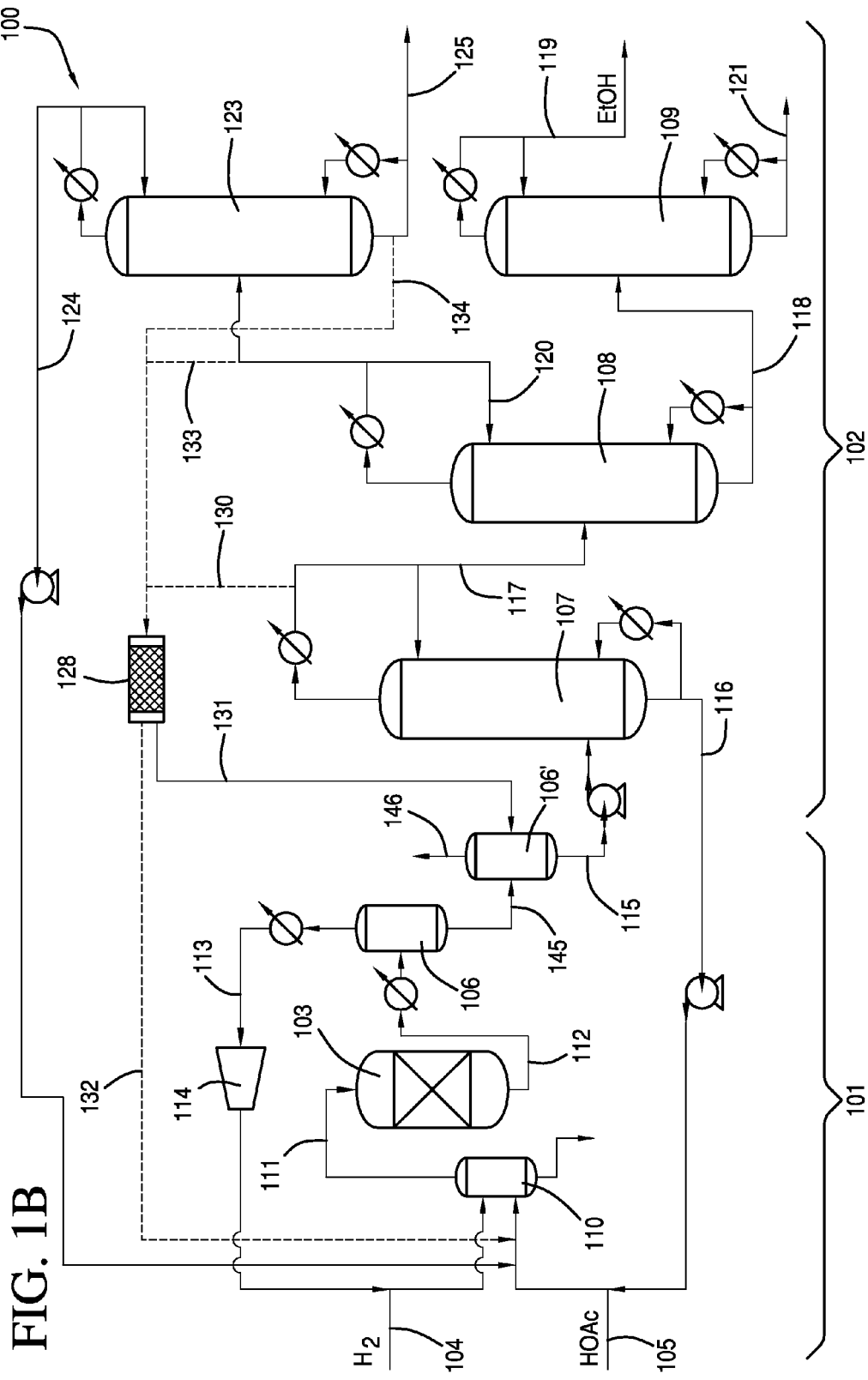
FIG. 1B is a schematic diagram of an ethanol production system having two flashers and an ion exchange resin reactor bed in accordance with one embodiment of the present invention.
Figure 2:
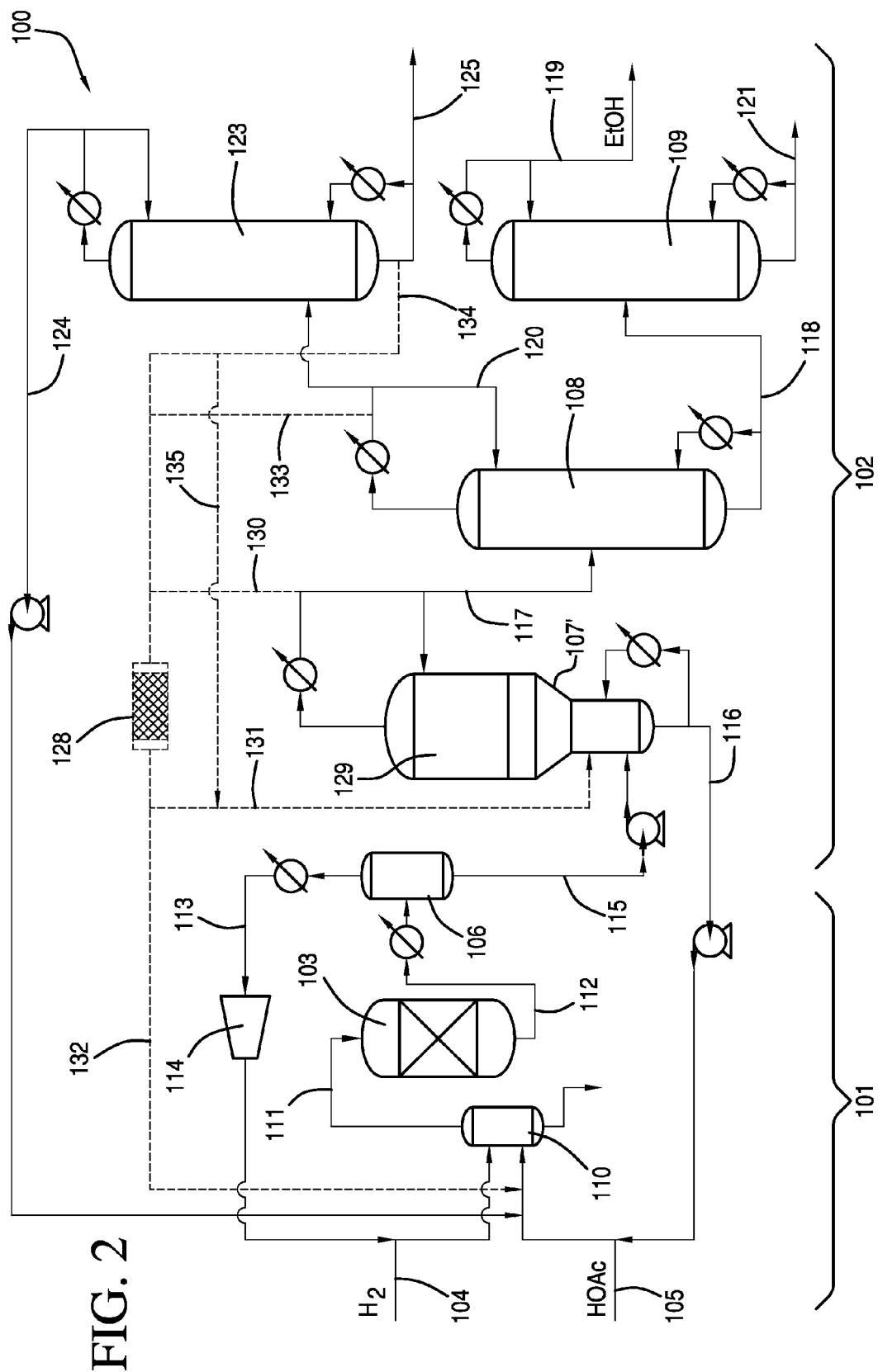
FIG. 2 is a schematic diagram of an ethanol production system having a column with a hydrolyzing section in accordance with one embodiment of the present invention.

FIGS. 1A, 1B and 2 show a hydrogenation system 100 suitable for the hydrogenation of acetic acid and separating ethanol from the crude reaction mixture according to one embodiment of the invention. System 100 comprises reaction zone 101 and distillation zone 102. Reaction zone 101 comprises reactor 103, hydrogen feed line 104 and acetic acid feed line 105. In FIGS. 1A and 1B, distillation zone 102 comprises flasher 106, first column 107, second column 108, third column 109, and fourth column 123. An ion exchange reactor bed 128 is also provided in FIGS. 1A and 1B. The ion exchange resin reactor bed 128 preferably is a gel or marcoreticular bed. One or more of the derivative streams may be fed to the ion exchange resin reactor bed 128 and the outflow of the reactor bed 128 may be directly or indirectly returned to the distillation zone 102 or reaction zone 101. In FIG. 1B, there are two flashers, 106 and 106'. In FIG. 2, the first column 107' comprises a hydrolyzing section 129, and an optional ion exchange reactor bed 128. Preferably, first column 107' is a reactive distillation column.

In one embodiment of the invention, a portion of the third residue from third column 109, which comprises water, may be fed to the ion exchange reactor bed 128 and/or the hydrolyzing section 129. Optionally the water fed to the ion exchange reactor bed 128 may also be obtained from an external source. The molar ratio of water to ethyl acetate fed to the hydrolysis unit is preferably at least 2:1, e.g., at least 5:1, at least 10:1 or at least 25:1.

Hydrogen and acetic acid are fed to a vaporizer 110 via lines 104 and 105, respectively, to create a vapor feed stream in line 111 that is directed to reactor 103. In one embodiment, lines 104 and 105 may be combined and jointly fed to the vaporizer 110, e.g., in one stream containing both hydrogen and acetic acid. The temperature of the vapor feed stream in line 111 is preferably from 100° C. to 350° C., e.g., from 120° C. to 310° C. or from 150° C. to 300° C. Any feed that is not vaporized is removed from vaporizer 110, as shown in FIG. 1A, and may be recycled thereto. In addition, although FIG. 1A shows line 111 being directed to the top of reactor 103, line 111 may be directed to the side, upper portion, or bottom of reactor 103. Further modifications and additional components to reaction zone 101 are described below.

Reactor 103 contains the catalyst that is used in the hydrogenation of the carboxylic acid, preferably acetic acid. In one embodiment, one or more guard beds (not shown) may be used to protect the catalyst from poisons or undesirable impurities contained in the feed or return/recycle streams. Such guard beds may be employed in the vapor or liquid streams. Suitable guard bed materials are known in the art and include, for example, carbon, silica, alumina, ceramic, or resins. In one aspect, the guard bed media is functionalized to trap particular species such as sulfur or halogens. During the hydrogenation process, a crude ethanol product stream is withdrawn, preferably continuously, from reactor 103 via line 112. The crude ethanol product stream may be condensed and fed to flasher 106, which, in turn, provides a vapor stream and a liquid stream. The flasher 106 in one embodiment preferably operates at a temperature of from 50° C. to 500° C., e.g., from 70° C. to 400° C. or from 100° C. to 350° C. In one embodiment, the pressure of flasher 106 preferably is from 50 KPa to 2000 KPa, e.g., from 75 KPa to 1500 KPa, or from 100 to 1000 KPa. In one preferred embodiment, the temperature and pressure of the flasher is similar to the temperature and pressure of the reactor 103.

The vapor stream exiting the flasher 106 may comprise hydrogen and hydrocarbons, which may be purged and/or returned to reaction zone 101 via line 113. As shown in FIG. 1A, the returned portion of the vapor stream passes through compressor 114 and is combined with the hydrogen feed and co-fed to vaporizer 110.

The liquid from flasher 106 is withdrawn and pumped via line 115 to the side of first column 107, also referred to as the acid separation column. In one embodiment, the contents of line 115 are substantially similar to the crude ethanol product obtained from the reactor, except that the composition has substantially no hydrogen, carbon dioxide, methane or ethane, which are removed by the flasher 106. Exemplary components of liquid in line 115 are provided in Table 2. It should be understood that liquid line 115 may contain other components, not listed, such as components in the feed.

TABLE 2

FEED COMPOSITION

| | Conc. (wt. %) | Conc. (wt. %) | Conc. (wt. %) |
|---|---|---|---|
| Ethanol | 5 to 70 | 10 to 60 | 15 to 50 |
| Acetic Acid | <90 | 5 to 80 | 15 to 70 |
| Water | 5 to 35 | 5 to 30 | 10 to 30 |
| Ethyl Acetate | <20 | 0.001 to 15 | 1 to 12 |
| Acetaldehyde | <10 | 0.001 to 3 | 0.1 to 3 |
| Acetal | <5 | 0.001 to 2 | 0.005 to 1 |
| Acetone | <5 | 0.0005 to 0.05 | 0.001 to 0.03 |
| Other Esters | <5 | <0.005 | <0.001 |
| Other Ethers | <5 | <0.005 | <0.001 |
| Other Alcohols | <5 | <0.005 | <0.001 |

The amounts indicated as less than (<) in the tables throughout present application are preferably not present and if present may be present in trace amounts or in amounts greater than 0.0001 wt. %.

The "other esters" in Table 2 may include, but are not limited to, ethyl propionate, methyl acetate, isopropyl acetate, n-propyl acetate, n-butyl acetate or mixtures thereof. The "other ethers" in Table 2 may include, but are not limited to, diethyl ether, methyl ethyl ether, isobutyl ethyl ether or mixtures thereof. The "other alcohols" in Table 2 may include, but are not limited to, methanol, isopropanol, n-propanol, n-butanol or mixtures thereof. In one embodiment, the feed composition, e.g., line 115, may comprise propanol, e.g., isopropanol and/or n-propanol, in an amount from 0.001 to 0.1 wt. %, from 0.001 to 0.05 wt. % or from 0.001 to 0.03 wt. %. In should be understood that these other components may be carried through in any of the distillate or residue streams described herein and will not be further described herein, unless indicated otherwise.

When the content of acetic acid in line 115 is less than 5 wt. %, the acid separation column 107 may be skipped and line 115 may be introduced directly to second column 108, also referred to herein as a light ends column.

In the embodiment shown in FIG. 1A, line 115 is introduced in the lower part of first column 107, e.g., lower half or lower third. In first column 107, unreacted acetic acid, a portion of the water, and other heavy components, if present, are removed from the composition in line 115 and are withdrawn, preferably continuously, as residue. Some or all of the first residue may be directly or indirectly returned and/or recycled back to reaction zone 101 via line 116. Recycling the acetic acid in line 116 to the vaporizer 110 may reduce the amount of heavies that need to be purged from vaporizer 110. Reducing the amount of heavies to be purged may improve efficiencies of the process while reducing byproducts. First column 107 also forms an overhead distillate, which is withdrawn in line 117, and which may be condensed and refluxed, for example, at a ratio of from 10:1 to 1:10, e.g., from 3:1 to 1:3 or from 1:2 to 2:1.

Any of columns 107, 108, 109, or 123 may comprise any distillation column capable of separation and/or purification. The columns preferably comprise tray columns having from 1 to 150 trays, e.g., from 10 to 100, from 20 to 95 trays or from 30 to 75 trays. The trays may be sieve trays, fixed valve trays, movable valve trays, or any other suitable design known in the art. In other embodiments, a packed column may be used. For packed columns, structured packing or random packing may be employed. The trays or packing may be arranged in one continuous column or they may be arranged in two or more columns such that the vapor from the first section enters the second section while the liquid from the second section enters the first section, etc.

The associated condensers and liquid separation vessels that may be employed with each of the distillation columns may be of any conventional design and are simplified in FIGS. 1A, 1B and 2. As shown in FIGS. 1A, 1B and 2, heat may be supplied to the base of each column or to a circulating bottom stream through a heat exchanger or reboiler. Other types of reboilers, such as internal reboilers, may also be used in some embodiments. The heat that is provided to reboilers may be derived from any heat generated during the process that is integrated with the reboilers or from an external source such as another heat generating chemical process or a boiler. Although one reactor and flasher are shown in FIG. 1A, additional reactors, flashers such as those shown in FIG. 1B, condensers, heating elements, and other components may be used in embodiments of the present invention. As will be recognized by those skilled in the art, various condensers, pumps, compressors, reboilers, drums, valves, connectors, separation vessels, etc., normally employed in carrying out chemical processes may also be combined and employed in the processes of the present invention.

The temperatures and pressures employed in any of the columns may vary. As a practical matter, pressures from 10 KPa to 3000 KPa will generally be employed in these zones although in some embodiments subatmospheric pressures may be employed as well as superatmospheric pressures. Temperatures within the various zones will normally range between the boiling points of the composition removed as the distillate and the composition removed as the residue. It will be recognized by those skilled in the art that the temperature at a given location in an operating distillation column is dependent on the composition of the material at that location and the pressure of column. In addition, feed rates may vary depending on the size of the production process and, if described, may be generically referred to in terms of feed weight ratios.

When column 107 is operated under standard atmospheric pressure, the temperature of the residue exiting in line 116 from column 107 preferably is from 95° C. to 120° C., e.g., from 105° C. to 117° C. or from 110° C. to 115° C. The temperature of the distillate exiting in line 117 from column 107 preferably is from 70° C. to 110° C., e.g., from 75° C. to 95° C. or from 80° C. to 90° C. In other embodiments, the pressure of first column 107 may range from 0.1 KPa to 510 KPa, e.g., from 1 KPa to 475 KPa or from 1 KPa to 375 KPa. Exemplary components of the distillate and residue compositions for first column 107 are provided in Table 3 below. It should also be understood that the distillate and residue may also contain other components, not listed, such as components in the feed. For convenience, the distillate and residue of the first column may also be referred to as the "first distillate" or "first residue." The distillates or residues of the other columns may also be referred to with similar numeric modifiers (second, third, etc.) in order to distinguish them from one another, but such modifiers should not be construed as requiring any particular separation order.

TABLE 3

| FIRST COLUMN | | | |
|---|---|---|---|
| | Conc. (wt. %) | Conc. (wt. %) | Conc. (wt. %) |
| Distillate | | | |
| Ethanol | 20 to 75 | 30 to 70 | 40 to 65 |
| Water | 10 to 40 | 15 to 35 | 20 to 35 |
| Acetic Acid | <2 | 0.001 to 0.5 | 0.01 to 0.2 |
| Ethyl Acetate | <60 | 5.0 to 40 | 10 to 30 |
| Acetaldehyde | <10 | 0.001 to 5 | 0.01 to 4 |
| Acetal | <0.1 | <0.1 | <0.05 |
| Acetone | <0.05 | 0.001 to 0.03 | 0.01 to 0.025 |
| Residue | | | |
| Acetic Acid | 60 to 100 | 70 to 95 | 85 to 92 |
| Water | <30 | 1 to 20 | 1 to 15 |
| Ethanol | <1 | <0.9 | <0.07 |

Without being bound by theory, the amount of ethyl acetate in the distillate may decrease due to the hydrolysis of the crude ethanol product and/or one or more derivative streams comprising ethyl acetate. In one embodiment, the amount of ethyl acetate fed to the first column 107 may decrease by at least 1%, e.g., at least 3% or 10%, compared to a feed where no hydrolysis of ethyl acetate occurs. In terms of ranges the decrease of ethyl acetate in the feed is from 1% to 85%, e.g., from 3% to 70% or from 10% to 55%. In another embodiment, the amount of ethanol fed to the first column 107 may increase by at least 0.5%, e.g., at least 2% or 4%, compared to a feed where no hydrolysis of ethyl acetate occurs. In terms of ranges the increase of ethanol in the feed is from 0.5% to 250%, e.g., from 2% to 200% or from 3% to 175%.

As shown in Table 3, without being bound by theory, it has surprisingly and unexpectedly been discovered that when any amount of acetal is detected in the feed that is introduced to the acid separation column (first column 107), the acetal appears to decompose in the column such that less or even no detectable amounts are present in the distillate and/or residue.

Depending on the reaction conditions, the crude ethanol product exiting reactor 103 in line 112 may comprise ethanol, acetic acid (unconverted), ethyl acetate, and water. After exiting reactor 103, a non-catalyzed equilibrium reaction may occur between the components contained in the crude ethanol product until it is added to flasher 106 and/or first column 107. This equilibrium reaction tends to drive the crude ethanol product to an equilibrium between ethanol/acetic acid and ethyl acetate/water, as shown below.

$$EtOH + HOAc \leftrightarrows EtOAc + H_2O$$

In the event the crude ethanol product is temporarily stored, e.g., in a holding tank, prior to being directed to distillation zone 102, extended residence times may be encountered. Generally, the longer the residence time between reaction zone 101 and distillation zone 102, the greater the formation of ethyl acetate. For example, when the residence time between reaction zone 101 and distillation zone 102 is greater than 5 days, significantly more ethyl acetate may form at the expense of ethanol. Thus, shorter residence times between reaction zone 101 and distillation zone 102 are generally preferred in order to maximize the amount of ethanol formed. In one embodiment, a holding tank (not shown), is included between the reaction zone 101 and distillation zone 102 for temporarily storing the liquid component from line 115 for up to 5 days, e.g., up to 1 day, or up to 1 hour. In a preferred embodiment no tank is included and the condensed liquids are fed directly to the first distillation column 107. In addition, the rate at which the non-catalyzed reaction occurs may increase as the temperature of the crude ethanol product, e.g., in line 115, increases. These reaction rates may be particularly problematic at temperatures exceeding 30° C., e.g., exceeding 40° C. or exceeding 50° C. Thus, in one embodiment, the temperature of liquid components in line 115 or in the optional holding tank is maintained at a temperature less than 40° C., e.g., less than 30° C. or less than 20° C. One or more cooling devices may be used to reduce the temperature of the liquid in line 115.

As discussed above, a holding tank (not shown) may be included between the reaction zone 101 and distillation zone 102 for temporarily storing the liquid component from line 115, for example from 1 to 24 hours, optionally at a temperature of about 21° C., and corresponding to an ethyl acetate formation of from 0.01 wt. % to 1.0 wt. % respectively. In addition, the rate at which the non-catalyzed reaction occurs may increase as the temperature of the crude ethanol product is increased. For example, as the temperature of the crude ethanol product in line 115 increases from 4° C. to 21° C., the rate of ethyl acetate formation may increase from about 0.01 wt. % per hour to about 0.005 wt. % per hour. Thus, in one embodiment, the temperature of liquid components in line 115 or in the optional holding tank is maintained at a temperature less than 21° C., e.g., less than 4° C. or less than −10° C.

The distillate, e.g., overhead stream, of column 107 optionally is condensed and refluxed as shown in FIG. 1A, preferably, at a reflux ratio of 1:5 to 10:1. The distillate in line 117 preferably comprises ethanol, ethyl acetate, and water, along with other impurities, which may be difficult to separate due to the formation of binary and tertiary azeotropes. In one optional embodiment of the invention, a portion of the distillate from line 117 may be directed to ion exchange reactor bed 128 via line 130. Optionally of a portion of the residue from third column 109, which comprises water, may also be directed to ion exchange reactor bed 128. In one embodiment, a portion of the distillate in line 130 may feed a reactive distillation column (not shown) to hydrolyze the ethyl acetate. This portion of the distillate is hydrolyzed to form a hydrolyzed stream, and the outflow stream of the ion exchange reactor bed 128 is directly or indirectly returned to the first column 107 via line 131. Exemplary indirect return methods may include storing or further treating the hydrolyzed stream in one or more additional columns to remove impurities prior to being sent to the first column 107 or reaction zone 101. The outflow in line 131 comprises acetic acid and ethanol, and preferably comprises less ethyl acetate than present in line 130. Preferably, the outflow in line 131 has at least 2% less ethyl acetate than line 130, e.g., at least 10% less or at least 20% less. In terms of ranges the amount of ethyl acetate in line 131 is less than line 130 by 2% to 25%, e.g., from 5 to 22% or from 7 to 20%. Preferably, the outflow in line 131 has at least 0.5% more ethanol than line 130, e.g., at least 2% more or at least 4% more. In terms of ranges the amount of ethanol in line 131 is more than line 130 by 0.5% to 20%, e.g., from 2 to 20% or from 4 to 20%. In addition, the outflow in line may also comprise less water than is present in line 130.

In one embodiment, the outflow in line 131 is co-fed with line 115 (not shown) or as shown in FIG. 1A the outflow in line 131 may be fed separately to the first column 107. The outflow in line 131 may be fed to a portion of the first column 107 such that the composition of the outflow is substantially similar to the composition of the liquid on the tray(s) in that portion of the first column 107.

In an optional embodiment, a portion of the outflow in line 132 may be directly or indirectly returned to the reaction zone 101. For example, the outflow in line 132 may be recycled with the first residue, which comprises acetic acid, in line 116 and returned to the reaction zone 101, e.g., returned to vaporizer 110, and/or reactor 103.

In a preferred embodiment, as shown in FIG. 1B, the outflow in line 131 is directly or indirectly fed to a low pressure flasher 106'. The system 100' in FIG. 1B comprises at least two flashers, e.g., flasher 106 and flasher 106'. The low pressure flasher 106' operates at a pressure from 0.1 KPa to 1000 KPa, e.g., from 0.1 KPa to 500 KPa or from 0.1 KPa to 100 KPa. In one embodiment, the pressure of low pressure flasher 106' preferably is at least 50 KPa lower than that of first flasher 106, e.g., at least 100 KPa lower or at least 200 KPa lower. The crude ethanol product is fed to the first flasher 106 via line 112. As discussed above, the vapor stream exiting the first flasher 106 comprises hydrogen and hydrocarbons, which may be purged and/or returned to reaction zone 101 via line 113. The remaining liquid in flasher 106 is withdrawn via line 145 and fed to a second flasher 106' to remove any residual vapor that is dissolved in the liquid. The remaining liquid in flasher 106' is withdrawn and pumped via line 115 to the side of the first column 107. Any vapors from flasher 106' may be flared via line 146.

Optionally the outflow in line 131 may be directly or indirectly sent to flasher 106 when the system 100 employs one flasher, such as in FIG. 1A.

The first distillate in line 117 is introduced to the second column 108, also referred to as the "light ends column," preferably in the middle part of column 108, e.g., middle half or middle third. As one example, when a 25 tray column is utilized in a column without water extraction, line 117 is introduced at tray 17. In one embodiment, the second column 108 may be an extractive distillation column. In such embodiments, an extraction agent, such as for example water, may be added to second column 108. If the extraction agent comprises water, it may be obtained from an external source or from an internal return/recycle line from one or more of the other columns.

Second column 108 may be a tray column or packed column. In one embodiment, second column 108 is a tray column having from 5 to 70 trays, e.g., from 15 to 50 trays or from 20 to 45 trays.

Although the temperature and pressure of second column 108 may vary, when at atmospheric pressure the temperature of the second residue exiting in line 118 from second column 108 preferably is from 60° C. to 90° C., e.g., from 70° C. to 90° C. or from 80° C. to 90° C. The temperature of the second distillate exiting in line 120 from second column 108 preferably is from 50° C. to 90° C., e.g., from 60° C. to 80° C. or from 60° C. to 70° C. Column 108 may operate at atmospheric pressure. In other embodiments, the pressure of second column 108 may range from 0.1 KPa to 510 KPa, e.g., from 1 KPa to 475 KPa or from 1 KPa to 375 KPa. Exemplary components for the distillate and residue compositions for second column 108 are provided in Table 4 below. It should be understood that the distillate and residue may also contain other components, not listed, such as components in the feed.

TABLE 4

SECOND COLUMN

|  | Conc. (wt. %) | Conc. (wt. %) | Conc. (wt. %) |
|---|---|---|---|
| Distillate |  |  |  |
| Ethyl Acetate | 10 to 90 | 25 to 90 | 50 to 90 |
| Acetaldehyde | 1 to 25 | 1 to 15 | 1 to 8 |
| Water | 1 to 25 | 1 to 20 | 4 to 16 |
| Ethanol | <30 | 0.001 to 15 | 0.01 to 5 |
| Acetal | <5 | 0.001 to 2 | 0.01 to 1 |
| Residue |  |  |  |
| Water | 30 to 70 | 30 to 60 | 30 to 50 |
| Ethanol | 20 to 75 | 30 to 70 | 40 to 70 |
| Ethyl Acetate | <3 | 0.001 to 2 | 0.001 to 0.5 |
| Acetic Acid | <0.5 | 0.001 to 0.3 | 0.001 to 0.2 |

The weight ratio of ethanol in the second residue to second distillate preferably is at least 3:1, e.g., at least 6:1, at least 8:1, at least 10:1 or at least 15:1. The weight ratio of ethyl acetate in the second residue to second distillate preferably is less than 0.4:1, e.g., less than 0.2:1 or less than 0.1:1. In embodiments that use an extractive column with water as an extraction agent as the second column 108, the weight ratio of ethyl acetate in the second residue to ethyl acetate in the second distillate approaches zero.

As shown in FIGS. 1A and 1B, the second residue from the bottom of second column 108, which comprises ethanol and water, is fed via line 118 to third column 109, also referred to as the "product column." More preferably, the second residue in line 118 is introduced in the lower part of third column 109, e.g., lower half or lower third. Third column 109 recovers ethanol, which preferably is substantially pure other than the azeotropic water content, as the distillate in line 119. The distillate of third column 109 preferably is refluxed as shown in FIGS. 1A and 1B, for example, at a reflux ratio of from 1:10 to 10:1, e.g., from 1:3 to 3:1 or from 1:2 to 2:1. The third residue in line 121, which preferably comprises primarily water, is preferably removed from the system 100 or may be partially directed to any portion of the system 100, preferably to hydrolysis units such as ion exchange reactor bed or reactive distillation column. Third column 109 is preferably a tray column as described above and preferably operates at atmospheric pressure. The temperature of the third distillate exiting in line 119 from third column 109 preferably is from 60° C. to 110° C., e.g., from 70° C. to 100° C. or from 75° C. to 95° C. The temperature of the third residue exiting from third column 109 preferably is from 70° C. to 115° C., e.g., from 80° C. to 110° C. or from 85° C. to 105° C. Exemplary components of the distillate and residue compositions for third column 109 are provided in Table 5 below. It should be understood that the distillate and residue may also contain other components, not listed, such as components in the feed.

TABLE 5

THIRD COLUMN

|  | Conc. (wt. %) | Conc. (wt. %) | Conc. (wt. %) |
|---|---|---|---|
| Distillate |  |  |  |
| Ethanol | 75 to 96 | 80 to 96 | 85 to 96 |
| Water | <12 | 1 to 9 | 3 to 8 |
| Acetic Acid | <1 | 0.001 to 0.1 | 0.005 to 0.01 |
| Ethyl Acetate | <5 | 0.001 to 4 | 0.01 to 3 |
| Residue |  |  |  |
| Water | 75 to 100 | 80 to 100 | 90 to 100 |
| Ethanol | <0.8 | 0.001 to 0.5 | 0.005 to 0.05 |
| Ethyl Acetate | <1 | 0.001 to 0.5 | 0.005 to 0.2 |
| Acetic Acid | <2 | 0.001 to 0.5 | 0.005 to 0.2 |

Any of the compounds that are carried through the distillation process from the feed or crude reaction product generally remain in the third distillate in amounts of less 0.1 wt. %, based on the total weight of the third distillate composition, e.g., less than 0.05 wt. % or less than 0.02 wt. %. In one embodiment, one or more side streams may remove impurities from any of the columns 107, 108 and/or 109 in the system 100. Preferably at least one side stream is used to remove impurities from the third column 109. The impurities may be purged and/or retained within the system 100.

The third distillate in line 119 may be further purified to form an anhydrous ethanol product stream, i.e., "finished anhydrous ethanol," using one or more additional separation systems, such as, for example, distillation columns (e.g., a finishing column) or molecular sieves.

Returning to second column 108, the second distillate preferably is refluxed as shown in FIGS. 1A and 1B, for example, at a reflux ratio of from 1:10 to 10:1, e.g., from 1:5 to 5:1 or from 1:3 to 3:1. In one optional embodiment, a portion of the second distillate from line 120, optionally along with any water from the residue of the third column 109, may be directed to the ion exchange reactor bed 128 via line 133. This portion of the distillate is hydrolyzed and the outflow of the ion exchange reactor bed 128 is directly or indirectly returned to the first column 107 via line 131 in FIG. 1A, to the low pressure flasher 106' in FIG. 1B, or to the reaction zone 101 via line 132. The outflow in line 131 comprises acetic acid and ethanol. Preferably, the outflow in line 131 has at least 3% less ethyl acetate than line 133, e.g., at least 8% less or at least 12% less. In terms of ranges, the amount of ethyl acetate in line 131 is less than that of line 132 by 3% to 25%, e.g., from 5 to 15% or from 6 to 12%. Preferably, the outflow in line 131 has at least 10% more ethanol, at least 30% more ethanol or at least 40% more ethanol than does line 133. In terms of ranges the amount of ethanol in line 131 is more than that of line 132 by 10% to 70%, e.g., from 15 to 70% or from 25 to 70%. In one embodiment, the outflow in line 131 is optionally co-fed with line 115 (not shown) to the first column 107 or separately fed to the first column 107 as shown.

In a preferred embodiment, the second distillate is fed via line 120 to fourth column 123, also referred to as the "acetaldehyde removal column" Alternatively, the second distillate in line 120 may be purged or returned to the reaction zone 101 without being separated in the acetaldehyde removal column. In fourth column 123, the second distillate in line 120 is separated into a fourth distillate, which comprises acetaldehyde, in line 124 and a fourth residue, which comprises ethyl acetate, in line 125. The fourth distillate preferably is refluxed at a reflux ratio of from 1:20 to 20:1, e.g., from 1:15 to 15:1 or from 1:10 to 10:1, and a portion of the fourth distillate is directly or indirectly returned to the reaction zone 101 as shown by line 124. For example, the fourth distillate may be combined with the acetic acid feed, added to the vaporizer 110, or added directly to the reactor 103. As shown, the fourth distillate is co-fed with the acetic acid in feed line 105 to vaporizer 110. Without being bound by theory, since acetaldehyde may be hydrogenated to form ethanol, the recycling of a stream that contains acetaldehyde to the reaction zone increases the yield of ethanol and decreases byproduct and waste generation. In another embodiment (not shown), the acetaldehyde may be collected and utilized, with or without further purification, to make useful products including but not limited to n-butanol, 1,3-butanediol, and/or crotonaldehyde and derivatives.

In one embodiment, a portion or all of the fourth residue, optionally along with any water from the residue of the third column 109, may be directed to the ion exchange reactor bed 128 via line 134. The portion or all of this residue may be hydrolyzed in the ion exchange reactor bed 128 and the outflow of the ion exchange reactor bed 128 may be directly or indirectly returned to the first column 107 via line 131 in FIG. 1A, to the low pressure flasher 106' in FIG. 1B, or to the reaction zone 101 via line 132. Preferably, the outflow in line 131 has at least 1% less ethyl acetate than that of line 134, e.g., at least 7% less or at least 10% less. In terms of ranges the amount of ethyl acetate in line 131 is less than that of line 132 by 1% to 25%, e.g., from 5 to 20% or from 6 to 15%. Preferably, the outflow in line 131 has at least 3% more, e.g., at least 6% more or at least 25% more, ethanol than does line 134. In terms of ranges the amount of ethanol in line 131 is more than that of line 132 by 3% to 50%, e.g., from 6 to 50% or from 25 to 50%. The outflow in line 131 comprises acetic acid and ethanol. In one embodiment, the outflow in line 131 is optionally co-fed with line 115 to the first column 107 or separately fed to the first column 107 as shown. It is preferred that at least one derivative stream from line 130, line 133 and/or line 134 is directed to the ion exchange reactor bed 128.

In one embodiment, at least 2% of the ethyl acetate in the first distillate is hydrolyzed, e.g., at least 10% or at least 20%. In one embodiment, at least 3% of the ethyl acetate in the second distillate is hydrolyzed, e.g., at least 8% or at least 12%. In one embodiment, at least 1% of the ethyl acetate in the fourth residue is hydrolyzed, e.g., at least 7% or at least 10%. In a preferred embodiment, the ion exchange reactor bed 128 is fed with the fourth residue via line 134. In an exemplary embodiment, 10% of the ethyl acetate in the first distillate and 50% of the ethyl acetate in the fourth residue may be hydrolyzed.

In one embodiment, the increase of ethanol in the hydrolyzed stream, as compared to the ethanol in the stream fed to the hydrolysis unit, is at least 0.5%, e.g., at least 2% or at least 4%. When the first distillate is hydrolyzed, the increase of ethanol is at least 0.5%, e.g., at least 2% or least 4%. When the second distillate is hydrolyzed, the increase of ethanol therein is at least 10% more, e.g., at least 30% more or least 40% more. When the fourth residue is hydrolyzed, the increase of ethanol therein is at least 3%, e.g., at least 6% or least 25%.

A portion of the fourth residue of fourth column 123 may also be purged via line 125. The fourth residue primarily comprises ethyl acetate and ethanol, and may be suitable for use as a solvent mixture or in the production of esters. In one preferred embodiment, the acetaldehyde is removed from the second distillate using fourth column 123 such that no detectable amount of acetaldehyde is present in the fourth residue in line 125.

Fourth column 123 is preferably a tray column as described above and preferably operates above atmospheric pressure. In one embodiment, the operating pressure is from 120 KPa to 5,000 KPa, e.g., from 200 KPa to 4,500 KPa, or from 500 KPa to 3,000 KPa. In a preferred embodiment, the fourth column 123 may operate at a pressure that is higher than the pressure of the other columns.

The temperature of the fourth distillate exiting in line 124 from fourth column 123 preferably is from 60° C. to 110° C., e.g., from 70° C. to 100° C. or from 75° C. to 95° C. The temperature of the residue exiting from fourth column 125 preferably is from 70° C. to 115° C., e.g., from 80° C. to 110° C. or from 85° C. to 110° C. Exemplary components of the distillate and residue compositions for fourth column 109 are provided in Table 6. It should be understood that the distillate and residue may also contain other components, not listed, such as components in the feed.

TABLE 6

| FOURTH COLUMN | | | |
|---|---|---|---|
| | Conc. (wt. %) | Conc. (wt. %) | Conc. (wt. %) |
| Distillate | | | |
| Acetaldehyde | 2 to 80 | 2 to 50 | 5 to 40 |
| Ethyl Acetate | <90 | 30 to 80 | 40 to 75 |
| Ethanol | <30 | 0.001 to 25 | 0.01 to 20 |
| Water | <25 | 0.001 to 20 | 0.01 to 15 |
| Residue | | | |
| Ethyl Acetate | 40 to 100 | 50 to 100 | 60 to 100 |
| Ethanol | <40 | 0.001 to 30 | 0 to 15 |
| Water | <25 | 0.001 to 20 | 2 to 15 |
| Acetaldehyde | <1 | 0.001 to 0.5 | Not detectable |
| Acetal | <3 | 0.001 to 2 | 0.01 to 1 |

As provided in Table 6, the amount of water in the fourth residue may be less than 25 wt. %, e.g., less than 15 wt. % or less than 5 wt. %. Hydrolyzing a portion of the fourth residue with such low water content is possible, but the hydrolysis may be increased through the addition of water to the fourth residue. The additional water may be provided by or recycled from one or more streams within the system, such as the third residue. The portion of the fourth residue to be hydrolyzed may, alternatively, be combined with the first distillate and/or second distillate, which may contain additional water or the portion of the fourth residue may be combined with an external source of water. The molar ratio of water to ethyl acetate fed to the hydrolysis unit is preferably at least 10:1, e.g., at least 20:1 or at least 25:1. For example, a molar excess of at least 10:1 water to ethyl acetate concentration in the one or more derivative streams to be hydrolyzed may increase the hydrolysis of ethyl acetate, and subsequently decrease the ethyl acetate concentration by at least 5%, e.g., at least 34% or at least 68%. A molar excess of at least 10:1 water to ethyl acetate preferably increases the ethanol in the hydrolyzed stream at least 14% or more, e.g., at least 90% or more, or at least 190% or more. A molar excess of at least 25:1 water to ethyl acetate concentration in the one or more derivative streams to be hydrolyzed may increase the hydrolysis of ethyl acetate, and subsequently decrease the ethyl acetate concentration by at least 10%, e.g., at least 52% or at least 83%. A molar excess of at least 25:1 water to ethyl acetate preferably increases the ethanol in the hydrolyzed stream at least 25% or more, e.g., at least 160% or more, or at least 230% or more. In an exemplary embodiment, a portion of the third residue in line 121 and all or a portion of the fourth residue in line 124 may be hydrolyzed.

Turning now to FIG. 2, the system 100 is similar to FIGS. 1A and 1B except that the first column 107' comprises a hydrolyzing section 129. The crude ethanol product produced in the reaction zone 101 is separated in flasher 106 and fed as a liquid stream via line 115 to first column 107'. Preferably first column 107' is a reactive distillation column. First column 107' may advantageously improve efficiency by reducing equipment use and energy consumption. In addition, first column 107' may also reduce the byproducts that may need to be purged from the system and reduce the amount of byproducts formed during distillation. Preferably, the distillate of first column 107' comprises a reduced amount of ethyl acetate as compared to a non-reactive distillation column, such as those shown in FIGS. 1A and 1B.

In one embodiment, hydrolyzing section 129 comprises an internal ion exchange reactor bed or catalysts used in ion exchange reactor beds. Preferably the ion exchange reactor bed or catalysts are located in the upper portion of first column 107'.

Optionally, one or more derivative streams in line 130, line 133, and/or line 134, or optionally a portion of line 121, may be directly or indirectly returned via lines 135 and 131 to the first column 107' to hydrolyze the contents. Preferably, the derivative streams that are recycled comprise ethyl acetate. In further embodiments, the one or more derivative streams in line 130, line 133, and/or line 134, or optionally a portion of line 121, optionally pass through the ion exchange reactor bed 128 before being returned to the first column 107' or optionally one or more of the flashers. In those embodiments, the outflow of the ion exchange reactor bed 128 or one or more distillations streams returned to the first column 107' may be fed with the liquid in line 115 or separately fed.

The finished ethanol composition obtained by the processes of the present invention preferably comprises from 75 to 96 wt. % ethanol, e.g., from 80 to 96 wt. % or from 85 to 96 wt. % ethanol, based on the total weight of the finished ethanol composition. Exemplary finished ethanol compositional ranges are provided below in Table 7.

TABLE 7

FINISHED ETHANOL COMPOSITIONS

| Component | Conc. (wt. %) | Conc. (wt. %) | Conc. (wt. %) |
|---|---|---|---|
| Ethanol | 75 to 96 | 80 to 96 | 85 to 96 |
| Water | <12 | 1 to 9 | 3 to 8 |
| Acetic Acid | <1 | <0.1 | <0.01 |
| Ethyl Acetate | <2 | <0.5 | <0.05 |
| Acetal | <0.05 | <0.01 | <0.005 |
| Acetone | <0.05 | <0.01 | <0.005 |
| Isopropanol | <0.5 | <0.1 | <0.05 |
| n-propanol | <0.5 | <0.1 | <0.05 |

The finished ethanol composition of the present invention preferably contains very low amounts, e.g., less than 0.5 wt. %, of other alcohols, such as methanol, butanol, isobutanol, isoamyl alcohol and other $C_4$-$C_{20}$ alcohols.

The finished ethanol composition produced by the embodiments of the present invention may be used in a variety of applications including fuels, solvents, chemical feedstocks, pharmaceutical products, cleansers, sanitizers, hydrogenation transport or consumption. In fuel applications, the finished ethanol composition may be blended with gasoline for motor vehicles such as automobiles, boats and small piston engine aircrafts. In non-fuel applications, the finished ethanol composition may be used as a solvent for toiletry and cosmetic preparations, detergents, disinfectants, coatings, inks, and pharmaceuticals. The finished ethanol composition may also be used as a processing solvent in manufacturing processes for medicinal products, food preparations, dyes, photochemicals and latex processing.

The finished ethanol composition may also be used a chemical feedstock to make other chemicals such as vinegar, ethyl acrylate, ethyl acetate, ethylene, glycol ethers, ethylamines, aldehydes, and higher alcohols, especially butanol. In the production of ethyl acetate, the finished ethanol composition may be esterified with acetic acid or reacted with polyvinyl acetate. The finished ethanol composition may be dehydrated to produce ethylene. Any of known dehydration catalysts can be employed in to dehydrate ethanol, such as those described in copending U.S. application Ser. No. 12/221,137 and U.S. application Ser. No. 12/221,138, the entire contents and disclosures of which are hereby incorporated by reference. A zeolite catalyst, for example, may be employed as the dehydration catalyst. Preferably, the zeolite has a pore diameter of at least about 0.6 nm, and preferred zeolites include dehydration catalysts selected from the group consisting of mordenites, ZSM-5, a zeolite X and a zeolite Y. Zeolite X is described, for example, in U.S. Pat. No. 2,882,244 and zeolite Y in U.S. Pat. No. 3,130,007, the entireties of which are hereby incorporated by reference.

In order that the invention disclosed herein may be more efficiently understood, an example is provided below. It should be understood that this example is for illustrative purposes only and is not to be construed as limiting the invention in any manner.

EXAMPLE 1

Examples of flow rates/compositions, ethyl acetate hydrolysis, and hydrolysis reactor sizing based on the lab-scale distillation train preliminary material balance data are discussed as follows. A system as shown in FIG. 1A was used.

The first distillate was removed from column at 10.2 g/min. The fourth distillate was removed from column at 1.67 g/min A mixture comprising 10% (1.02 g/min.) of the first distillate from first column 107 and 50% (0.685 g/min.) of the fourth residue from fourth column 123 was fed to first column 107. The mixture had an initial $H_2O$:EtOAc molar ratio of 2.56:1.0 with the potential for hydrolysis of 26.3% of the ethyl acetate contained in this mixture.

As shown in Table 8, the potential EtOAc hydrolysis described in this example would be equivalent to approximately a 10.6% reduction in the amount of EtOAc contained in the first column overhead (based on 0.199 g/min delta EtOAc via hydrolysis compared to a first column overhead EtOAc flow rate of 1.88 g/min). This example of combined recycle stream would increase the first column loading by 8.4% (based on 1.68 g/min recycle stream flow rate and 20 g/min first column feed rate).

This example was performed on a lab-scale recycle stream at 1.68 g/min (~100 g/hour). It would be expected to use an approximately a 100 ml ion-exchange reactor bed to achieve a 1 BV/hour feed rate (at density of ~1 g/ml).

TABLE 8

EtOAc HYDROLYSIS POTENTIAL

|  |  | EtOAc | H₂O | EtOH | HOAc |
|---|---|---|---|---|---|
|  | M.W. | 88 | 18 | 46 | 60 |
| First Column Distillate |  |  |  |  |  |
|  | wt. % | 18.47 | 34.99 | 43.84 | 0.018 |
|  | g/min. | 1.884 | 3.569 | 4.472 | 0.0018 |
| 10% of distillate | g/min. | 0.1884 | 0.3569 | 0.4472 | 0.00018 |
|  | Molality | 2.099 | 19.439 | 9.530 | 0.003 |
| Fourth Column Residue |  |  |  |  |  |
|  | wt. % | 83.2 | 5.784 | 12 | 0.071 |
|  | g/min. | 1.137 | 0.0791 | 0.165 | 0.001 |
| 50% of residue | g/min. | 0.569 | 0.040 | 0.0825 | 0.0005 |
|  | Molality | 9.455 | 3.213 | 2.6087 | 0.0118 |
| Mixture |  | 44.954 | 23.546 | 31.460 | 0.0406 |
|  | wt. % |  |  |  |  |
|  | g/min | 0.7569 | 0.3965 | 0.5297 | 0.0007 |
|  | Molality | 5.108 | 13.081 | 6.839 | 0.0068 |
| H₂O/EtOAc ratio | Molality |  | 2.561 |  |  |
| Δ EtOAc, x | Molality | 1.342 |  |  |  |
| Δ EtOAc |  |  |  | 0.199 |  |
| Equilibrium | wt. % | 33.144 | 21.130 | 37.633 | 8.0926 |
| Equilibrium | g/min | 0.558 | 0.356 | 0.634 | 0.1363 |
| Equilibrium | Molality | 3.766 | 11.739 | 8.181 | 1.3488 |

EXAMPLE 2

A crude ethanol product comprising ethanol, acetic acid, water and ethyl acetate was produced by reacting a vaporized feed comprising 95.2 wt. % acetic acid and 4.6 wt. % water with hydrogen in the presence of a catalyst comprising 1.6 wt. % platinum and 1 wt. % tin supported on ⅛ inch calcium silicate modified silica extrudates at an average temperature of 291° C., an outlet pressure of 2,063 KPa. Unreacted hydrogen was recycled back to the inlet of the reactor such that the total H₂/acetic acid molar ratio was 5.8 at a GHSV of 3,893 hr⁻¹. Under these conditions, 42.8% of the acetic acid was converted, and the selectivity to ethanol was 87.1%, selectivity to ethyl acetate was 8.4%, and selectivity to acetaldehyde was 3.5%. The crude ethanol product was purified using a separation scheme having distillation columns as shown in FIG. 1.

The crude ethanol product was fed to the first column at a feed rate of 20 g/min. The composition of the liquid feed is provided in Table 9. The first column is a 2 inch diameter Oldershaw with 50 trays. The column was operated at a temperature of 115° C. at atmospheric pressure. Unless otherwise indicated, a column operating temperature is the temperature of the liquid in the reboiler and the pressure at the top of the column is ambient (approximately one atmosphere). The column differential pressure between the trays in the first column was 7.4 KPa. The first residue was withdrawn at a flow rate of 12.4 g/min and returned to the hydrogenation reactor.

The hydrolysis potential of the first distillate of the first column is shown in Table 9. Ethyl acetate hydrolysis potential is calculated based on varying percentages of reaching the theoretical hydrolysis equilibrium reaction rate of K=0.25. Starting concentration of reactants and products present in stream are used to calculate molar equivalents. The theoretical K is used to calculate the molar equivalents that would be present at chemical equilibrium.

TABLE 9

| Distillate | First Distillate (conc. wt %) | 100% potential (conc. wt %) | 50% potential (conc. wt %) | 10% potential (conc. wt %) |
|---|---|---|---|---|
| Water | 24.9 | 23.2 | 23.9 | 24.7 |
| Acetic Acid | 0.08 | 2.9 | 1.7 | 0.4 |
| Ethanol | 53.7 | 55.8 | 54.9 | 53.9 |
| Ethyl Acetate | 20.2 | 16.1 | 17.8 | 19.7 |
| Others | 1.1 | 1.2 | 1.2 | 1.2 |

As shown in Table 9, the potential ethyl acetate hydrolysis of the first distillate fed to an ion exchange reactor utilizing strongly acidic resin would be equivalent to approximately a 21% reduction at 100% hydrolysis potential, 12% reduction at 50% hydrolysis potential or 2% reduction at 10% hydrolysis potential. Each of these hydrolysis potentials demonstrates a reduction in the amount of ethyl acetate contained in the first distillate.

EXAMPLE 3

The first distillate of Example 2 was condensed and refluxed at a 1:1 ratio at the top of the first column, and a portion of the distillate was introduced to the second column at a feed rate of 7.6 g/min. The second column is a 2 inch diameter Oldershaw design equipped with 25 trays. The second column was operated at a temperature of 82° C. at atmospheric pressure. The column differential pressure between the trays in the second column was 2.6 KPa. The second residue was withdrawn at a flow rate of 5.8 g/min and directed to the third column. The second distillate was refluxed at a ratio of 4.5:0.5.

The hydrolysis potential of the second distillate of the second column is shown in Table 10.

TABLE 10

| Distillate | Second Distillate (conc. wt %) | 100% potential (conc. wt %) | 50% potential (conc. wt %) | 10% potential (conc. wt %) |
|---|---|---|---|---|
| Water | 7.2 | 3.4 | 4.4 | 6.2 |
| Acetic Acid | 0.03 | 6.3 | 4.6 | 1.6 |
| Ethanol | 11.7 | 16.5 | 15.2 | 12.9 |
| Ethyl Acetate | 79.8 | 70.6 | 73.9 | 77.5 |
| Others | 1.3 | 1.3 | 1.3 | 1.3 |

As shown in Table 10, the potential ethyl acetate hydrolysis of the second distillate fed to an ion exchange reactor utilizing strongly acidic resin would be equivalent to approximately a 12% reduction at 100% hydrolysis potential, 8% reduction at 50% hydrolysis potential or 3% reduction at 10% hydrolysis potential. Each of these hydrolysis potentials demonstrates a reduction in the amount of ethyl acetate contained in the first distillate.

EXAMPLE 4

The fourth column is a 1 inch diameter Oldershaw column containing 25 trays and designed to operate at elevated pressures. The fourth column was operated at a pressure of 25 psig, and the differential pressure between the trays in the fourth column was 2.2 KPa. The fourth distillate was refluxed at a ratio of 28:1 and returned to the hydrogenation reactor. The residue of the fourth column was withdrawn at a flow rate of 1.6 g/min.

The hydrolysis potential of the fourth residue of the fourth column is shown in Table 11.

TABLE 11

| Distillate | Fourth Residue (conc. wt %) | 100% potential (conc. wt %) | 50% potential (conc. wt %) | 10% potential (conc. wt %) |
|---|---|---|---|---|
| Water | 6.3 | 3.1 | 5.6 | 5.9 |
| Acetic Acid | 0.03 | 5.3 | 1.2 | 0.7 |
| Ethanol | 14.6 | 18.7 | 15.5 | 15.1 |
| Ethyl Acetate | 80.9 | 73.1 | 79.1 | 79.9 |
| Others | 1.3 | 1.3 | 1.3 | 1.3 |

As shown in Table 11, the potential ethyl acetate hydrolysis of the fourth residue fed to an ion exchange reactor utilizing strongly acidic resin would be equivalent to approximately a 10% reduction at 100% hydrolysis potential, 7% reduction at 50% hydrolysis potential or 1% reduction at 10% hydrolysis potential. Each of these hydrolysis potentials demonstrates a reduction in the amount of ethyl acetate contained in the first distillate.

EXAMPLE 5

Residue from the second column was introduced above the 25th tray to the third column, a 2 inch Oldershaw containing 60 trays, at a rate of 10 g/min. The third column was operated at a temperature of 103° C. at standard pressure. The column differential pressure between the trays in the third column was 6.2 KPa. The third residue was withdrawn at a flow rate of 2.7 g/min. The third distillate was condensed and refluxed at a 3:1 ratio at the top of the third column. The third residue that mainly comprised water was collected.

The water in the fourth residue is increased adding a portion of the third residue to the fourth residue. The molar ratio of water to ethyl acetate is 10:1. The hydrolysis potential of the combined fourth residue and third residue is shown in Table 12.

TABLE 12

| Distillate | Fourth Residue and Third Residue (conc. wt %) | 100% potential (conc. wt %) | 50% potential (conc. wt %) | 10% potential (conc. wt %) |
|---|---|---|---|---|
| Water | 63.4 | 54.8 | 59.1 | 62.8 |
| Acetic Acid | 0.01 | 14.3 | 7.2 | 1.1 |
| Ethanol | 5.6 | 16.6 | 11.1 | 6.4 |
| Ethyl Acetate | 31.0 | 10.0 | 20.5 | 29.5 |
| Others | 0 | 0 | 0 | 0 |

As shown in Table 12, the potential ethyl acetate hydrolysis of the fourth residue fed to an ion exchange reactor utilizing strongly acidic resin with a 10:1 molar excess of water sourced from third residue would be equivalent to approximately a 68% reduction at 100% hydrolysis potential, 34% reduction at 50% hydrolysis potential or 5% reduction at 10% hydrolysis potential. Each of these hydrolysis potentials demonstrates a reduction in the amount of ethyl acetate contained in the first distillate.

EXAMPLE 6

Using the same conditions as Example 5, except that the molar ratio of water to ethyl acetate is 25:1. The hydrolysis potential of the combined fourth residue and third residue is shown in Table 13.

TABLE 13

| Distillate | Fourth Residue and Third Residue (conc. wt %) | 100% potential (conc. wt %) | 50% potential (conc. wt %) | 10% potential (conc. wt %) |
|---|---|---|---|---|
| Water | 81.2 | 75.8 | 77.9 | 80.6 |
| Acetic Acid | 0.01 | 9.0 | 7.2 | 1.1 |
| Ethanol | 2.9 | 9.8 | 7.7 | 3.7 |
| Ethyl Acetate | 15.9 | 2.7 | 5.6 | 14.4 |
| Others | 0 | 0 | 0 | 0 |

An increase in the molar excess to 25:1 water to ethyl acetate would decrease the ethyl acetate concentration in the fourth residue to approximately a 83% reduction at 100% hydrolysis potential, 52% reduction at 50% hydrolysis potential or 10% reduction at 10% hydrolysis potential as fed over a strongly acidic ion exchange resin.

While the invention has been described in detail, modifications within the spirit and scope of the invention will be readily apparent to those of skill in the art. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A process for purifying a crude ethanol product, comprising the steps of:
   hydrogenating acetic acid in a reactor in the presence of a catalyst to form the crude ethanol product;
   separating at least a portion of the crude ethanol product in a first column into a first distillate comprising ethanol, water and ethyl acetate, and a first residue comprising acetic acid;
   separating at least a portion of the first distillate in a second column into a second distillate comprising ethyl acetate and less than 30 wt. % ethanol, and a second residue comprising ethanol and water;
   optionally separating at least a portion of the second residue in a third column into a third distillate comprising ethanol and a third residue comprising water;
   optionally separating at least a portion of the second distillate in a fourth column into a fourth distillate comprising acetaldehyde and a fourth residue comprising ethyl acetate;
   hydrolyzing at least a portion of one of the first distillate, the second distillate, or the fourth residue to form a hydrolyzed stream; and
   feeding at least a portion of the hydrolyzed stream to the first column.

2. The process of claim 1, wherein the step of hydrolyzing is conducted under liquid phase conditions.

3. The process of claim 1, wherein the at least a portion of the first distillate is hydrolyzed to form the hydrolyzed stream.

4. The process of claim 1, wherein the at least a portion of the second distillate is hydrolyzed to form the hydrolyzed stream.

5. The process of claim 1, wherein the at least a portion of the fourth residue is hydrolyzed to form the hydrolyzed stream.

6. The process of claim 1, wherein a portion of the first distillate and a portion of the fourth residue are hydrolyzed to form the hydrolyzed stream.

7. The process of claim 1, wherein the hydrolyzed stream comprises acetic acid and ethanol.

8. The process of claim 7, wherein the at least a portion of one of the first distillate, the second distillate, or the fourth residue that is hydrolyzed has a molar ratio of water to ethyl acetate of at least 10:1.

9. The process of claim 1, wherein the at least a portion of one of the first distillate or the second distillate is hydrolyzed in the presence of a strongly acidic heterogeneous or homogenous catalyst.

10. The process of claim 1, wherein the at least a portion of one of the first distillate or the second distillate is hydrolyzed in an ion exchange reactor bed.

11. The process of claim 10, wherein the ion exchange reactor bed is located externally from the first column, second column and third column.

12. The process of claim 10, wherein at least a portion of the third residue is fed to the ion exchange reactor bed.

13. A process for purifying a crude ethanol product, comprising the steps:
providing the crude ethanol product comprising ethanol, water, acetic acid, and ethyl acetate;
separating at least a portion of the crude ethanol product in a first column into a first distillate comprising ethanol, water and ethyl acetate, and a first residue comprising acetic acid;
separating at least a portion of the first distillate in a second column into a second distillate comprising ethyl acetate and less than 30 wt. % ethanol, and a second residue comprising ethanol and water;
optionally separating at least a portion of the second residue in a third column into a third distillate comprising ethanol and a third residue comprising water;
optionally separating at least a portion of the second distillate in a fourth column into a fourth distillate comprising acetaldehyde and a fourth residue comprising ethyl acetate;
hydrolyzing at least a portion of the second distillate; or the fourth residue to form a hydrolyzed stream; and
feeding at least a portion of the hydrolyzed stream to the first column.

14. The process of claim 13, wherein the step of hydrolyzing is conducted under liquid phase conditions.

15. The process of claim 13, wherein the at least a portion of the second distillate is hydrolyzed to form the hydrolyzed stream.

16. The process of claim 13, wherein the at least a portion of the fourth residue is hydrolyzed to form the hydrolyzed stream.

17. The process of claim 13, wherein the hydrolyzed stream comprises acetic acid and ethanol.

18. The process of claim 13, wherein the at least a portion of the second distillate; or the fourth residue that is hydrolyzed has a molar ratio of water to ethyl acetate of at least 10:1.

19. The process of claim 13, wherein the at least a portion of the second distillate is hydrolyzed in the presence of a strongly acidic heterogeneous or homogenous catalyst.

20. The process of claim 13, wherein the at least a portion of the second distillate is hydrolyzed in an ion exchange reactor bed.

21. The process of claim 20, wherein the ion exchange reactor bed is located externally from the first column, second column and third column.

22. The process of claim 20, wherein at least a portion of the third residue is fed to the ion exchange reactor bed.

23. A process for purifying a crude ethanol product, comprising the steps of:
hydrogenating acetic acid in a reactor in the presence of a catalyst to form the crude ethanol product;
hydrolyzing at least a portion of the crude ethanol product in a first column; and
separating at least a portion of the crude ethanol product in the first column into a first distillate comprising ethanol, water and a reduced amount of ethyl acetate, and a first residue comprising acetic acid.

24. The process of claim 23, wherein the first column comprises a hydrolyzing section.

25. The process of claim 23, wherein the first column comprises an internal ion exchange reactor bed resin.

26. The process of claim 23, wherein the first column is a reactive distillation column.

27. The process of claim 23, wherein the first column comprises a strongly acidic heterogeneous or homogenous catalyst.

28. The process of claim 23, further comprising separating at least a portion of the first distillate in a second column into a second distillate comprising ethyl acetate and a second residue comprising ethanol and water.

29. The process of claim 28, further comprising separating at least a portion of the second residue in a third column into a third distillate comprising ethanol and a third residue comprising water.

30. The process of claim 29, further comprising separating at least a portion of the second distillate in a fourth column into a fourth distillate comprising acetaldehyde and a fourth residue comprising ethyl acetate.

31. The process of claim 30, further comprising hydrolyzing at least a portion of one of the first distillate, the second distillate, or fourth residue to form a hydrolyzed stream.

32. The process of claim 31, wherein at least a portion of the fourth residue is hydrolyzed to form the hydrolyzed stream.

33. The process of claim 31, wherein at least a portion of the hydrolyzed stream is directly or indirectly fed to the first column.

34. The process of claim 31, wherein at least a portion of the hydrolyzed stream is directly or indirectly returned to a flasher, wherein the flasher separates the crude ethanol product into a vapor stream and a liquid stream.

35. A process for hydrolyzing ethyl acetate, comprising:
hydrogenating acetic acid in a reactor in the presence of a catalyst to form a crude ethanol product;
hydrolyzing the crude ethanol product in a hydrolysis unit under conditions effective to form a hydrolyzed stream comprising less ethyl acetate than the ethyl acetate-containing stream;
feeding at least a portion of the hydrolyzed stream to a first column;
separating at least a portion of the crude ethanol product in the first column into a first distillate comprising ethanol, water and ethyl acetate, and a first residue comprising acetic acid;
separating at least a portion of the first distillate in a second column into a second distillate comprising ethyl acetate and less than 30 wt. % ethanol, and a second residue comprising ethanol and water;

separating at least a portion of the second residue in a third column into a third distillate comprising ethanol and a third residue comprising water; and optionally separating at least a portion of the second distillate in a fourth column into a fourth distillate comprising acetaldehyde and a fourth residue comprising ethyl acetate.

36. The process of claim 35, wherein the hydrolyzed stream comprises at least 1% less ethyl acetate than the ethyl acetate-containing stream.

37. The process of claim 35, wherein the hydrolyzed stream comprises at least 10% less ethyl acetate than the ethyl acetate-containing stream.

38. The process of claim 35, wherein the hydrolyzed stream comprises at least 0.5% more ethanol than the ethyl acetate-containing stream.

* * * * *